(12) United States Patent
Kraft et al.

(10) Patent No.: US 8,776,786 B2
(45) Date of Patent: Jul. 15, 2014

(54) PULSE DRUG NEBULIZATION SYSTEM, FORMULATIONS THEREFORE, AND METHODS OF USE

(75) Inventors: Edward R Kraft, Galveston, TX (US); Perenlai Enkhbaatar, Galveston, TX (US); Daniel S Traber, Galveston, TX (US); Gabriela A. Kulp, Santa Fe, TX (US)

(73) Assignee: The Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/423,044

(22) Filed: Mar. 16, 2012

(65) Prior Publication Data
US 2012/0174915 A1    Jul. 12, 2012

Related U.S. Application Data

(62) Division of application No. 11/855,870, filed on Sep. 14, 2007, now abandoned.

(60) Provisional application No. 60/845,087, filed on Sep. 15, 2006, provisional application No. 60/891,128, filed on Feb. 22, 2007.

(51) Int. Cl.
*A61M 11/00* (2006.01)
*A61M 15/00* (2006.01)
*A61M 16/10* (2006.01)

(52) U.S. Cl.
USPC ............. 128/200.22; 128/200.23; 128/203.12

(58) Field of Classification Search
USPC ............. 128/200.14, 200.18, 200.21–200.23, 128/203.15, 203.12; 222/635, 389, 394, 222/386.5, 402.1, 400.8, 399
See application file for complete search history.

(56) References Cited

U.S. PATENT DOCUMENTS

| 4,783,008 A | 11/1988 | Ikeuchi et al. |
|---|---|---|
| 5,156,776 A | 10/1992 | Loedding et al. |
| 5,438,982 A | 8/1995 | Macintyre |
| 5,642,730 A | 7/1997 | Baran |

(Continued)

FOREIGN PATENT DOCUMENTS

| GB | 2316022 | 2/1998 |
|---|---|---|
| WO | 974896 | 12/1997 |

OTHER PUBLICATIONS

Atkins, P. "Dry Powder Inhalers: An Overview." Respiratory Care, 2005, vol. 50, No. 10, p. 1304-1312.

(Continued)

*Primary Examiner* — Kristen Matter
(74) *Attorney, Agent, or Firm* — Wong Cabello Lutsch Rutherford & Brucculeri, LLP

(57) ABSTRACT

Liquid nebulizer apparatus, systems, and formulation compositions, as well as systems for the nebulized, aerosol delivery of such compositions, for the administration and insufflation of medicinal aerosols into the pulmonary system of a mammal are described. The nebulizing apparatus and system can effectively aerosolize a variety of viscosities of medicinal liquid drug carriers, including those made up of oil, water, or emulsions of oil and water. Drugs dissolved or suspended in the compositions and formulations described and adapted for use herein are not damaged or denatured by the nebulization process when the nebulizer described is used. Further, the nebulization system itself can be adapted for use with both mechanically assisted pulmonary ventilation systems as well as hand-held inhalers and nose/mouth face masks for use in pulmonary drug delivery.

19 Claims, 16 Drawing Sheets

(56) References Cited

U.S. PATENT DOCUMENTS

| | | | |
|---|---|---|---|
| 5,694,929 A * | 12/1997 | Christopher | 128/207.14 |
| 5,725,153 A | 3/1998 | Wang et al. | |
| 5,752,663 A | 5/1998 | Fischer et al. | |
| 5,868,322 A | 2/1999 | Loucks, Jr. et al. | |
| 5,884,846 A * | 3/1999 | Tan | 239/338 |
| 5,964,223 A | 10/1999 | Baran | |
| 6,032,876 A | 3/2000 | Bertsch et al. | |
| 6,079,413 A | 6/2000 | Baran | |
| 6,125,844 A | 10/2000 | Samiotes | |
| 6,161,536 A | 12/2000 | Redmon et al. | |
| 6,526,976 B1 | 3/2003 | Baran | |
| 6,729,334 B1 | 5/2004 | Baran | |
| 7,117,867 B2 * | 10/2006 | Cox et al. | 128/200.14 |
| 7,913,686 B2 * | 3/2011 | Hughes et al. | 128/200.14 |
| 8,261,747 B2 * | 9/2012 | Smaldone et al. | 128/207.14 |
| 2003/0144219 A1 | 7/2003 | Phinney et al. | |
| 2005/0121025 A1 | 6/2005 | Garnard et al. | |
| 2005/0249822 A1 | 11/2005 | Pilkiewicz et al. | |
| 2006/0162722 A1 * | 7/2006 | Boehm et al. | 128/200.14 |
| 2008/0142002 A1 * | 6/2008 | Fink et al. | 128/200.14 |

OTHER PUBLICATIONS

Boulet, L., et al. "Canadian Asthma consensus report, 1999" Canadian Medical Association Journal, Nov. 30, 1999, 11 Suppl, p. 1-S62.
Cryan, S. "Carrier-based Strategies for Targeting Protein and Peptide Drugs to the Lungs" The AAPS Journal 2005, vol. 7, No. 1, Article 4, p. E20-E41.
Delong, M., et al. "Dose Delivery Characteristics of the AIR Pulmonary Delivery System Over a Range of Inspiratory Flow Rates." Journal of Aerosol Medicine, 2005, vol. 18, No. 4, p. 452-459.
Dhand, R. "New Nebuliser Technology—Aerosol Generation by Using a Vibrating Mesh or Plate with Multiple Apertures" Report for Omron Healthcare, Inc., p. 1-4. published in 2003ad.
Enkhbaatar, P. et al. "The Inducible Nitric Oxide Synthase Inhibitor BBS-2 Prevents Acute lung Injury in Sheep after Burn and Smoke Inhalation Injury." American Journal of Respiratory and Critical Care Medicine, 2003, vol. 167, p. 1021-1026.
Enkhbaatar, P. et al. "Aerosolized Tissue Plasminogen Inhibitor Improves Pulmonary Function in Sheep with Burn and Smoke Inhalation" Shock, 2004, vol. 22, No. 1, p. 70-75.
Fink, J. and Dhand, R. "Bronchodilator Resuscitation in the Emergency Department: Part 1 of 2: Device Selection." Respiratory Care, Nov. 1999, vol. 44, No. 11, p. 1353-1374.
Fink, J. "Aerosol Delivery to Ventilated Infant and Pediatric Patients." Respiratory Care, Jun. 2004, vol. 49, No. 6, p. 653-665.
Hamahata, A et al. "Gamma-Tocopheral Nebulization by a Lipid Aerosolization Device Improves Pulmonary Function in Sheep with Burn and Smoke Inhalation Injury" Free Radic Biol Med (2008) 45(4):425-433.
Hybertson, B. et al. "Aerosol-Administered x-Tocopherol Attenuates lung Inflammation in Rats Given Lipopolysaccharide Intratracheally" Experimental lung Research, 2005, vol. 31, p. 283-294.
Kim, K., et al. "Heliox-Driven Albuterol Nebulization for Asthma Exacerbations: An Overview" Respiratory Care, Jun. 2006, vol. 51, No. 6, p. 613-618.
Laube, B. "The Expanding Role of Aerosols in Systemic Drug Delivery, Gene Therapy, and Vaccination." Respiratory Care, Sep. 2005, vol. 50, No. 9, p. 1161-1174.
Morita, N. et al. "Aerosolized Alpha-Tocopherol Ameliorates Acute Lung Injury Following Combined Burn and Smoke Inhalation Injury in Sheep" Shock 25 (3) (2006) 277-282.
Noto, T., et al. "Potentiation of Penile Tumescence by T-1032, a New Potent and Specific Phosphodiesterase Type V Inhibitor, in Dogs." The Journal of Pharmacology and Experimental Therapeutics, 2000, vol. 294, No. 3, p. 870-875.
Wright, J., et al. "Inhaler devices for the management of asthma and COPD." Effective Health Care, 2003, vol. 8, No. 1., p. 1-12.
International Search Report for Corresponding International Patent Application No. PCT/US20071020072.
Written Opinion for Corresponding International Patent Application No. PCT/US20071020072.

* cited by examiner

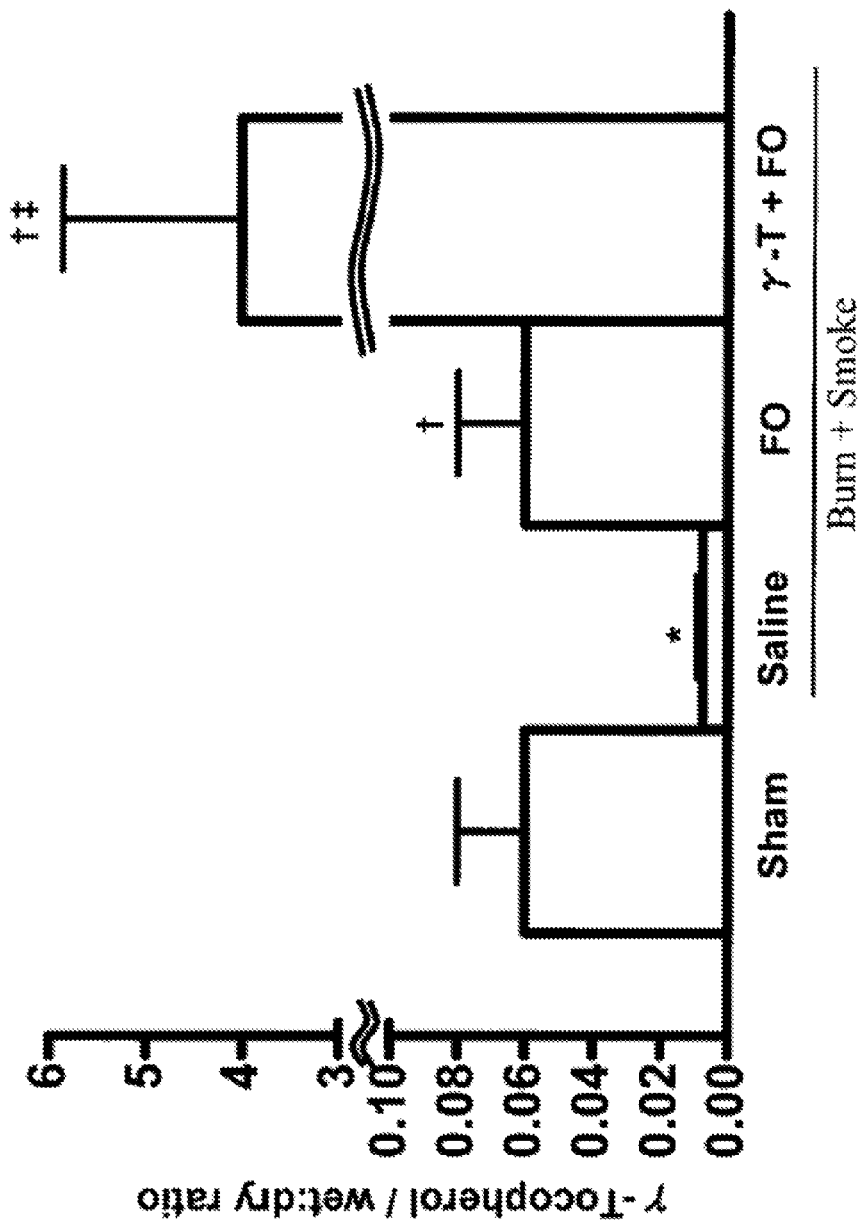
FIG. 9 γ-Tocopherol concentration in lung tissue.
Data are expressed as mean±SEM.
* $p < 0.05$ vs. Sham; † $p < 0.05$ vs. Saline; ‡ $p < 0.05$ vs. FO.

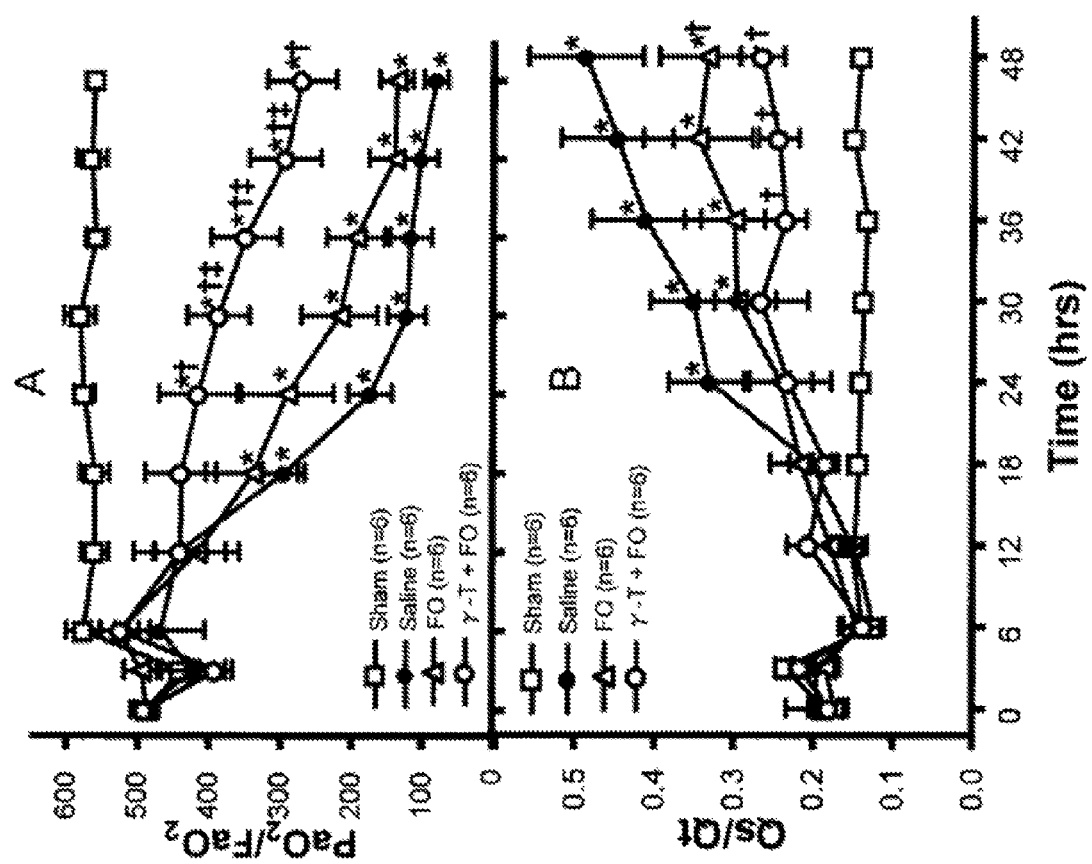
FIG. 10 Effect of γ-T nebulization on $PaO_2/FiO_2$ (A) and pulmonary shunt fraction (B). Data are expressed as mean ± SEM. * $p < 0.05$ vs. Sham; † $p < 0.05$ vs. Saline; ‡ $p < 0.05$ vs. FO.

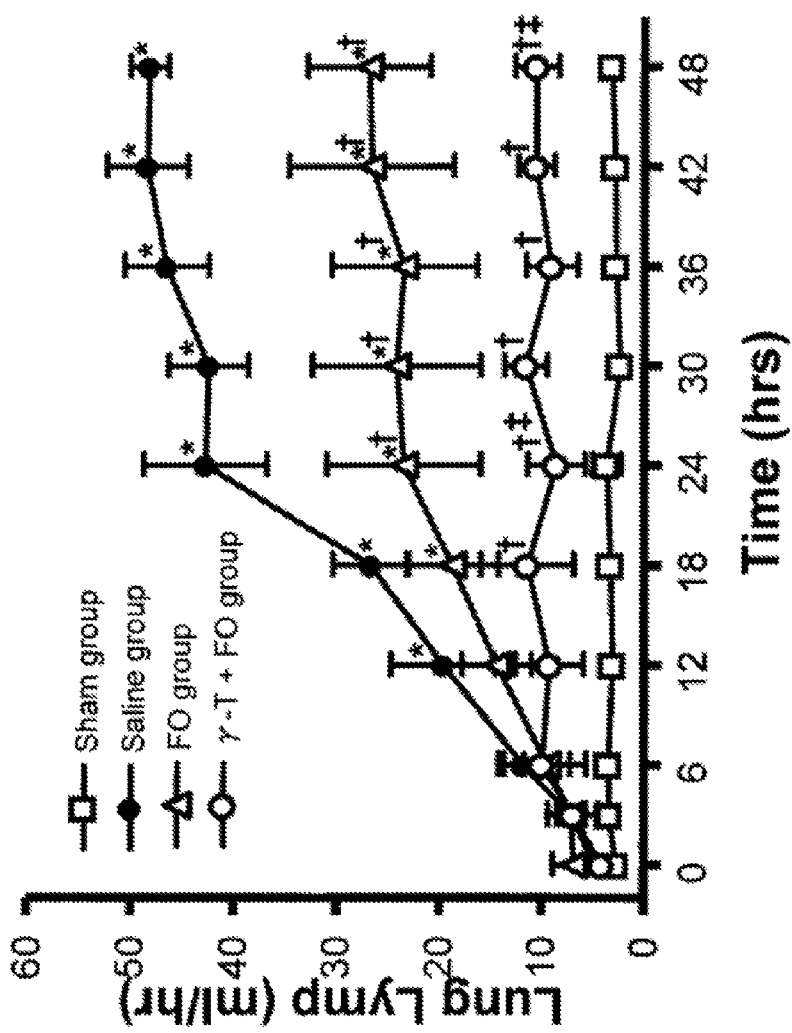
FIG. 11 Effect of γ-T nebulization on lung lymph flow (pulmonary transvascular fluid flux). Data are expressed as mean±SEM.
* $p < 0.05$ vs. Sham; † $p < 0.05$ vs. Saline; ‡ $p < 0.05$ vs. FO.

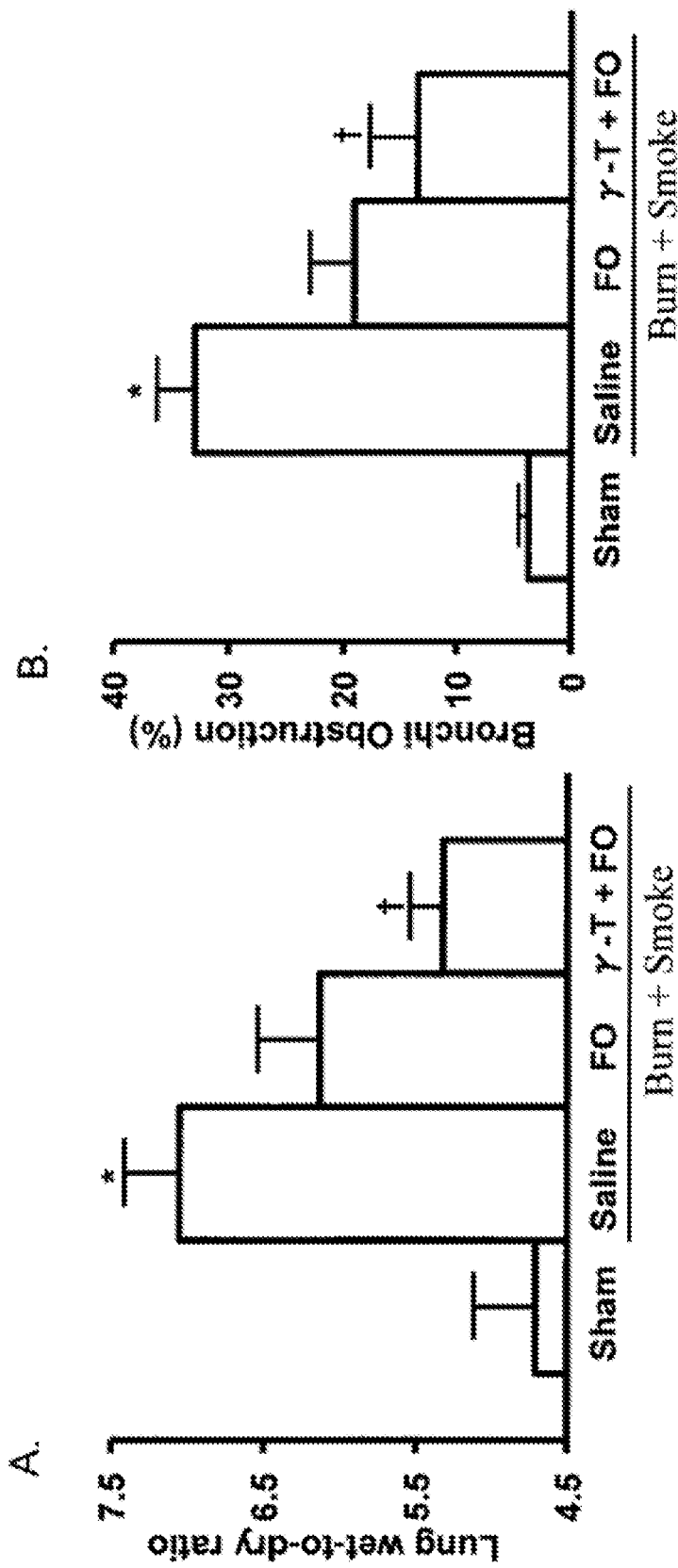
FIG. 12 Effect of γ-T nebulization on lung wet-to-dry ratio (A) and airway obstruction (B). The lung histology was evaluated by pathologist to determine the percentage of airway obstruction. Data are expressed as mean±SEM. * $p < 0.05$ vs. Sham; † $p < 0.05$ vs. Saline.

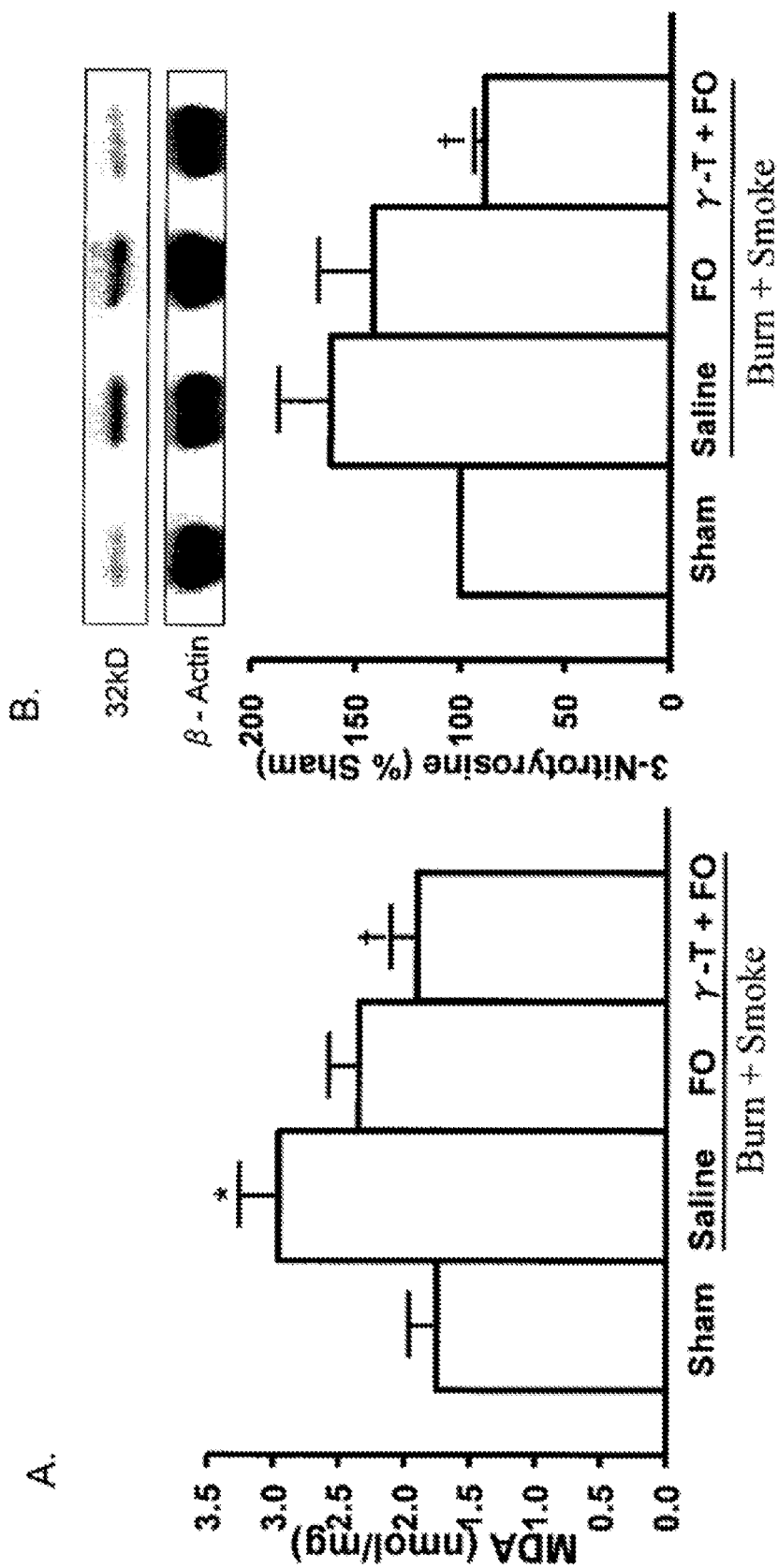
FIG. 13 Effect of γ-T nebulization on Malondialdehyde (MDA) Level (A) and 3-Nitrotyrosine in lung tissue (B). Data are expressed as mean±SEM. † $p < 0.05$ vs. Saline.

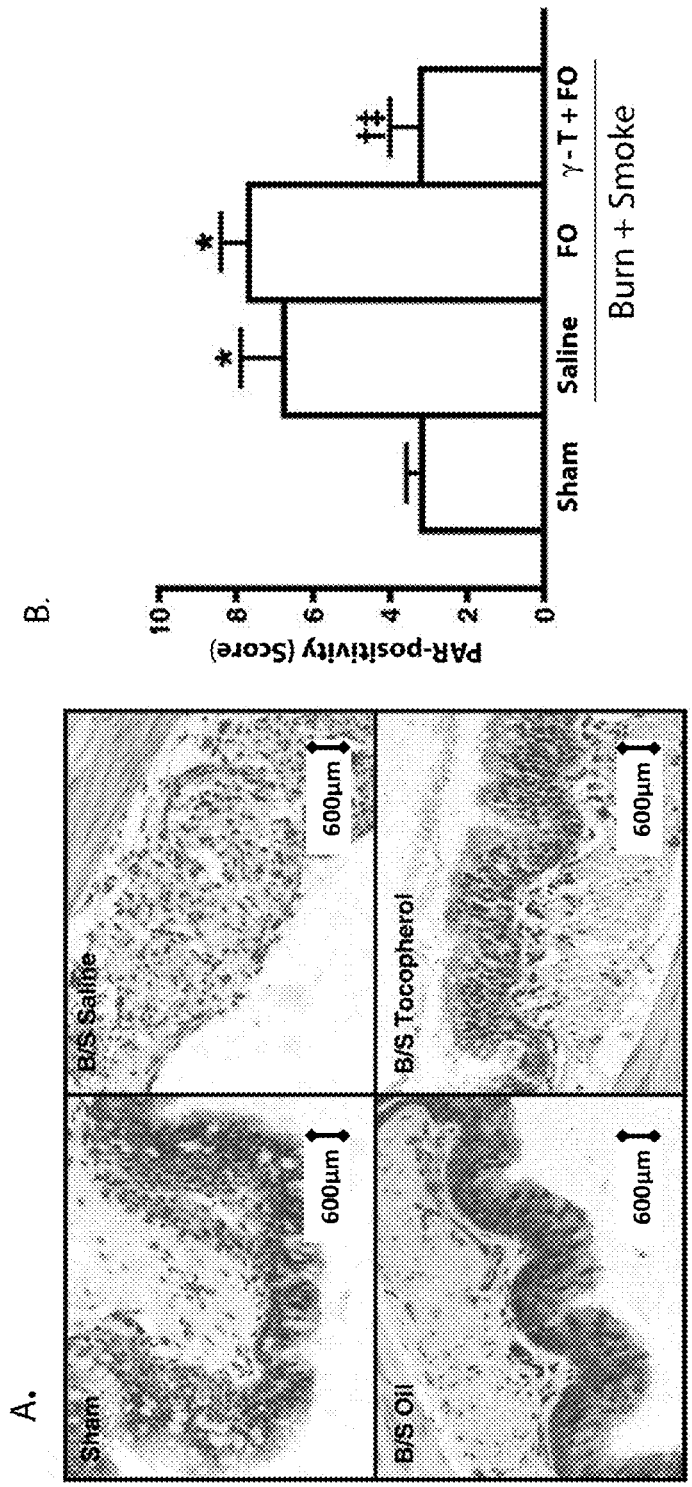
FIG 14 Effect of γ-T nebulization on Poly (ADP-ribose) Polymerase Activity in lung tissue. Immunohistochemistry (A). PAR-positivity Score (B) Data expressed as mean ± SEM.
* $p<0.05$ vs Sham, † $p<0.05$ vs. Saline, ‡ $p<0.05$ vs. FO

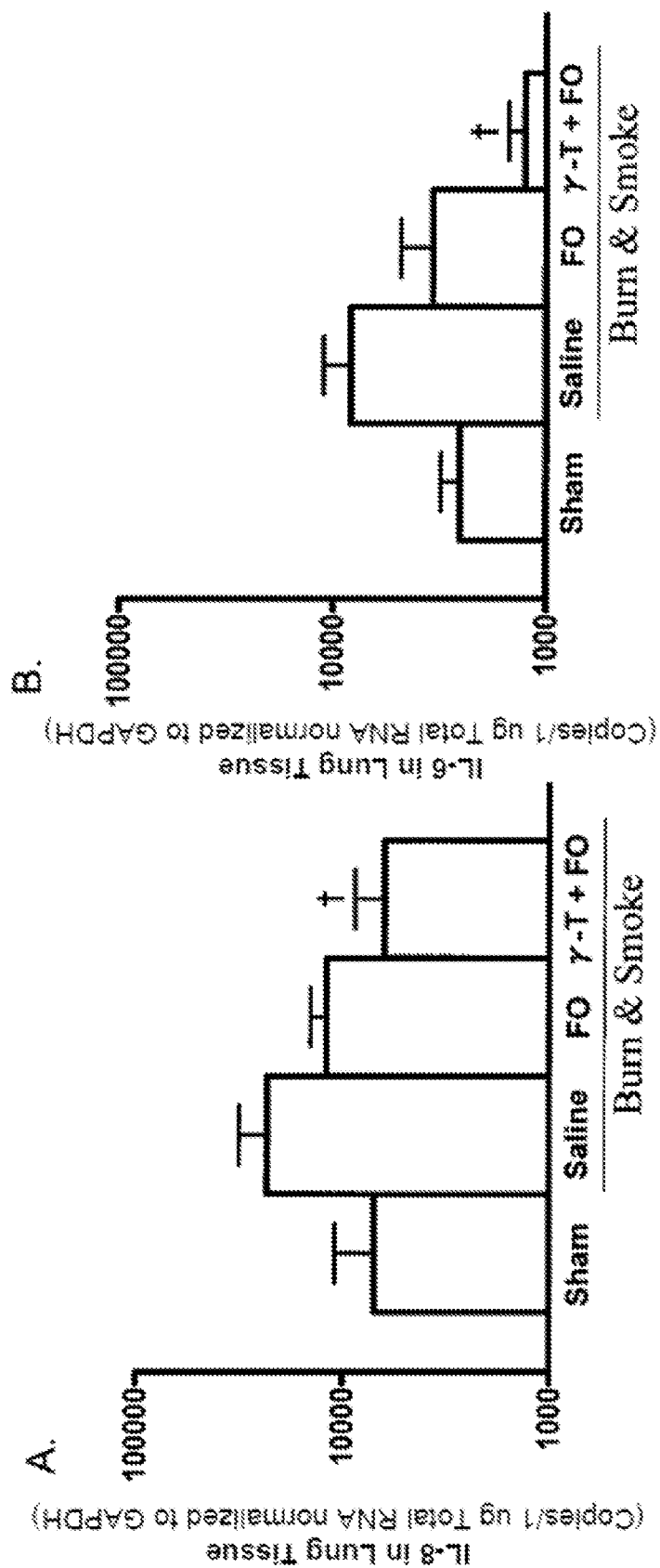
FIG. 15 Effect of γ-T nebulization on IL-8(A), IL-6(B) mRNA in lung tissue. Data are expressed as mean±SEM. † p < 0.05 vs. Saline.

PULSE DRUG NEBULIZATION SYSTEM, FORMULATIONS THEREFORE, AND METHODS OF USE

CROSS REFERENCE TO RELATED APPLICATIONS

The present application is a divisional of, and claims priority to, U.S. patent application Ser. No. 11/855,870 filed Sep. 14, 2007, now abandoned, which in turn claims priority to U.S. Provisional Patent Application Ser. No. 60/845,087, filed Sep. 15, 2006, and U.S. Provisional Patent Application Ser. No. 60/891,128, filed Feb. 22, 2007, the contents of all of which are incorporated herein by reference in their entirety.

STATEMENT REGARDING GOVERNMENT INTERESTS

The government may own rights in the present invention pursuant to grant number 1 P01 GM066312-01A2 from the National Institute of Health.

FIELD OF THE INVENTION

The present invention relates to compositions, formulations and methods for the treatment and prevention of cytoxicity, cell damage and inflammation in the pulmonary system of patients, as well as systems for use in delivering such compositions and formulations to the patient. More particularly, the present invention relates to tocopherol compositions and formulations for use in the treatment of pulmonary disorders in patients, methods for their use, and systems for the delivery of such tocopherol-containing compositions and formulations to the pulmonary region of a patient.

BACKGROUND OF THE INVENTION

Burn inhalation injury of the lungs increases morbidity and mortality, with 70% of victims of smoke inhalation dying within the first 12 hours of [Shirani, K. Z., et al., *Ann. Surg., Vol.* 205(1): pp. 82-87 (1987)]. Lung injury is traumatic, and is typically caused by heat and chemical irritation, with chemical injury being the leading lethal cause of smoke inhalation injury. Similarly, thermally injured patients who sustain inhalation injury have a 20 fold increase in mortality [see, Saffle, J. R., et al., *J. Burn Care Rehabil.*, Vol. 16(3, pt. 1); pp. 219-232 (1995)].

Injury from burn and smoke inhalation has been demonstrated to produce a systemic inflammatory response and increase levels of reactive oxygen species (ROS) [Traber, D. L., et al., *Burns Inc. Therm. Inj.*, Vol. 14(5): pp. 357-364 (1988)]. ROS produces an increase in pulmonary microvasculature and pulmonary edema accompanied by increased lipid peroxidation in lung tissue. Inhibition of lipid peroxidation has been demonstrated to reduce these symptoms in animals subjected to hot sawdust smoke by Z. Min, et al., [*J. Med. Cell. PLA*, Vol. 5(2): pp. 176-180 (1990)].

Antioxidants are compounds that reduce oxidation products and have been demonstrated to reduce cytotoxicity in smoke inhalation-lung injury, adult respiratory distress syndrome, emphysema and asthma. More recently it has been reported that the use of antioxidants such as vitamin E may be beneficial in the treatment of victims of fire accidents who sustain both thermal injury to the skin and smoke inhalation and exhibit evidence of oxidant injury [Morita, N., et al., *Shock*, Vol. 25(3): pp. 277-282 (2006)]. For example, vitamin C and vitamin E (alpha-tocopherol and gamma tocopherol) are antioxidants in vivo which may act together to scavenge ROS to produce non-reactive compounds within the human body. One of the important chemical features of the tocopherols is that they are redox agents which act under certain circumstances as antioxidants. In acting as an antioxidant, tocopherols presumably prevent the formation of toxic oxidation products, such as perioxidation products formed from unsaturated fatty acids. Further, it has recently been discovered that individual members in the class of tocopherols may exhibit different biological properties from one another despite their structural similarity. Some investigators, for example, believe that γ-tocopherol, unlike α-tocopherol, acts in vivo as a trap for membrane-soluble electrophilic nitrogen oxides and other electrophilic mutagens [Christen, S., et al. *Proc. Natl. Acad. Sci.* 94: 3217-3222 (1997]. Vitamin E is remarkably safe, and falls within a class of compounds that are "generally regarded as safe" or "GRAS". Vitamin E is available in several forms that present varied activities between them. Whereas alpha-tocopherol has been widely investigated for therapeutic uses, until recently gamma-tocopherol (a form of "des-methyl tocopherol") has received much less attention in science. However, gamma-tocopherol presents a variety of beneficial advantages over alpha-tocopherol in various considerations. In one particular regard, gamma-tocopherol has been characterized to exhibit much more potent anti-oxidant qualities, resulting in a unique anti-inflammatory activity not shared with the alpha-tocopherol. In addition, gamma-tocopherol is believed to enhance outcomes of therapy when combined with certain other bioactive agents or drugs. Antioxidants, and in particular, gamma tocopherol is capable of preserving the elastase inhibitor capacity of the lower respiratory tract fluid of mammals exposed to harmful, chemical gases. Thus, it is believed that the direct delivery of antioxidants such as vitamin E, and particularly, gamma tocopherol directly to the airways of mammals, may reduce or treat the injury resulting from burn and smoke inhalation, as well as other pulmonary disorders.

Inhalation-based therapies have been extensively evaluated as site-specific method to treat pulmonary disorders due to their ability to rapidly and selectively deposit agents in the lung in greater amounts than can be readily achieved by other methods [see: Kuhn, R. J., *Pharmacotherapy*, Vol. 22: pp. 80S-85S (2002)]. Consequently, a variety of aerosolized compounds have been researched and their aerosolization attempted, including recombinant proteins, glutathione, and vitamins such as Vitamin E [Hybertson, B. M., et al., *Free Radic. Biol. Med.*, Vol. 18: pp. 537-542 (1995)]. However, these attempts have been largely unsuccessful due to the substantial insolubility of these therapeutic agents and potential therapeutic agents in carrier systems that are suitable for use in aerosol therapeutic delivery systems. For example, many of the pharmaceutical compounds, vitamins, and biological agents that exhibit promise in the treatment of pulmonary diseases, disorders and damage that result from smoke inhalation are insoluble in water and other the carriers for aerosol formulation and for use in nebulizers. Further, these same compounds which exhibit potential therapeutic applicability in the pulmonary region of patients are often soluble only in oil-based solvents or compounds, and as such they are unable to be aerosolized by the current nebulizer systems available and in use. In the event that such oil-based formulations can be realized, and they can be transformed into an aerosol by a nebulizer, the exceedingly high flow rate required to aerosolize them, and the resultant particle size of the aerosols makes the formulations unsuitable for use in treatment. Consequently, not only are new formulations necessary, but a new nebulizer design is required in order to convert formulations of such therapeutic agents into aerosols having the desired particle size in the desired range of 2 µm to 12 µm.

The present invention meets these needs by providing novel, pharmaceutical compositions of tocopherols, such as gamma tocopherol, and tocopherol derivatives which are demonstrated herein to protect animals from cytotoxic injury and death, pulmonary injury, as well as other injuries and disease conditions, including inflammatory diseases, as well as methods and systems for delivering these compositions by way of nebulizing such water-insoluble drug formulations.

BRIEF SUMMARY OF THE INVENTION

In one aspect of the present disclosure, an apparatus for nebulizing a non-aqueous liquid is described.

In accordance with another aspect of the present disclosure, a nebulization system comprising a nebulizing nozzle capable of nebulizing a composition comprising fatty acids or lipids is described, wherein the nebulizing nozzle comprises an outer gas-delivery tube and an inner microchannel delivery tube having a central fluid channel, wherein the outer delivery tube is concentrically configured around the inner delivery tube, such concentric configuration forming an annular intermediate space between the two tubes, and wherein the intermediate air space between the two tubes is the free air opening value, the value of which is the internal diameter of the outer gas-delivery tube minus the total inside diameter of the inner microchannel delivery tube.

In accordance with another aspect of the present disclosure, a pulmonary drug delivery system capable of nebulizing a composition comprising a water-insoluble or substantially water-insoluble drug and a fatty acid or lipid is described, wherein the system comprises a reservoir for containing the drug composition; a reservoir for containing a propellant gas; a mechanical control valve capable of regulating the flow of the propellant gas and the drug composition; and a nebulizing nozzle adapted to receive both the drug composition and the propellant gas, wherein the nebulizing nozzle can produce aerosol droplets having a particle size ranging from about 2 µm to about 12 µm in median mass aerodynamic size.

In another aspect of the present disclosure, formulations for nebulization of water-insoluble drugs are provided.

In another aspect of the present disclosure, methods of delivering formulations of water-insoluble drugs via nebulizer are provided.

In one aspect of the present disclosure, a pharmaceutical kit for aerosol administration of a medicament is described.

In a further aspect of the present disclosure, methods for preparing formulations for nebulization are described.

In yet another aspect of the present disclosure, the use of antioxidants in combination with one or more fatty acids or lipids in the preparation of a medicament comprising gamma tocopherol for the treatment of pulmonary disorders is described.

In another aspect of the present disclosure, the use of compositions comprising gamma-tocopherol are described for use in reducing the levels of reactive oxygen species in the pulmonary microvasculature of a patient.

In a further aspect of the present disclosure, the use of alpha or gamma-tocopherol in the manufacture of a medicament for the inhibition of lipid peroxidation in the pulmonary system of a patient is described.

In further aspects of the present disclosure, a non-aqueous medicinal aerosol composition is described, the composition comprising a therapeutically effective amount of an inhibitor of c-GMP-specific phosphodiesterase (PDE) type IV or type V, or a derivative, metabolite, solvate, prodrug, or polymorph thereof, and a lipid or fatty acid. In accordance with this aspect of the present disclosure, the inhibitor of c-GMP PDE IV or PDE V may be sildenafil, or a derivative, metabolite, prodrug, polymorph, or solvate thereof, in a therapeutically-effective amount ranging from about 1 mg/kg/day to about 1,000 mg/kg/day.

In accordance with further aspects of the present disclosure, a drug nebulizing apparatus adapted for pulmonary inhalation and delivery of aerosolized medicaments into a mammalian patient is described, wherein the apparatus comprises a reservoir containing a drug formulation and a nebulizing nozzle adapted to be fit to a breathing circuit and further attached to a face mask, wherein the nebulizing nozzle produces aerosolized droplets sized for pulmonary, inhaled drug delivery of the drug formulation, and wherein the nebulizing nozzle comprises a fluid micro-tube with an air delivery tube capable of nebulizing a fluid from the micro-tube into droplets into droplets sized for inhaled drug delivery. In accordance with this aspect of the disclosure, the drug formulation may be in the form of a mixture, a solution, a suspension, or an emulsion, and the droplets may range in size from about 2 µm to about 10 µm, including from about 2 µm to about 5 µm. In further accordance with this aspect of the disclosure, the face mask is typically capable of being fit to the patient's nose, mouth, or both the nose and the mouth.

In accordance with yet another aspect of the present disclosure, a face mask for use in a pressurized drug delivery system is provided, the face mask comprising an at least partially deformable body having a surface for placement against a face of a patient and a nose bridge section formed in an upper section of the body, a vent to the atmosphere outside of the face mask, and a connector integral to a portion of the mask, the connector defining a fluid pathway into an interior portion of the face mask and constructed to receive, under pressure, an aerosolized drug composition. In association with this aspect, the face mask may be coupled to a nebulizer drug delivery system for delivering an aerosolized drug through the face mask. Further, the body of the face mask may include a bottommost surface for contacting the face when the face mask is applied against the face and the body at least partially deforms.

In one embodiment, the pharmaceutical compositions of the present invention comprises gamma tocopherol measured at about 5% to about 10% (w/v). In one embodiment, pharmaceutical compositions of the present invention comprise gamma tocopherol measured at about 10% to about 15% (w/v). In one embodiment, pharmaceutical compositions of the present invention comprise gamma tocopherol measured at about 15% to about 20% (w/v). In one embodiment, pharmaceutical compositions of the present invention comprise gamma tocopherol measured at about 20% to about 25% (w/v). In a preferred embodiment, the pharmaceutical compositions of the present invention comprise gamma tocopherol measured at about 10% (w/v).

In one embodiment, methods of preparing pharmaceutical compositions of the present invention further comprise adjusting the osmolarity of the pharmaceutical composition to an osmolarity in the range from about 200 to about 400 mOsmol/L. In one embodiment, the osmolarity of the pharmaceutical composition is in the range from about 240 to about 360 mOsmol/L or an isotonic range.

In one embodiment of the present disclosure, the pH of the tocopherol compositions, in particular the gamma tocopherol composition, is in the range from about 2 to about 9, while in other embodiments, the pH may be in the range from about 3 to about 8. The pH of the pharmaceutical composition may be adjusted to a physiologically compatible range. For example, in one embodiment, the pH of the pharmaceutical compositions described herein may be in the range from about 3.0 to about 7.5. In another embodiment, the pharmaceutical compositions of the present invention may have a pH in the range from about 3.5 to about 7.5.

In one embodiment, storage of the gamma tocopherol pharmaceutical composition is about three months, and the storage temperature is in the range from about 15° C. to about 30° C., and more preferably in the range from about 20° C. to about 25° C. In another embodiment, storage of the gamma tocopherol pharmaceutical composition is about six months, and the storage temperature is in the range from about 15° C. to about 30° C., and more preferably in the range from about 20° C. to about 25° C. In another embodiment, storage of the gamma tocopherol pharmaceutical composition is about twelve months, and the storage temperature is in the range from about 15° C. to about 30° C., and more preferably in the range from about 20° C. to about 25° C.

The present invention further includes kits comprising tocopherol and tocopherol compositions in accordance with the present disclosure. In accordance with further aspects of this embodiment, the present disclosure contemplates and includes kits comprising gamma tocopherol and γ-tocopherol pharmaceutical compositions of the present invention. In certain embodiments, such kits may comprise one or more containers to store the gamma tocopherol pharmaceutical compositions.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1A:
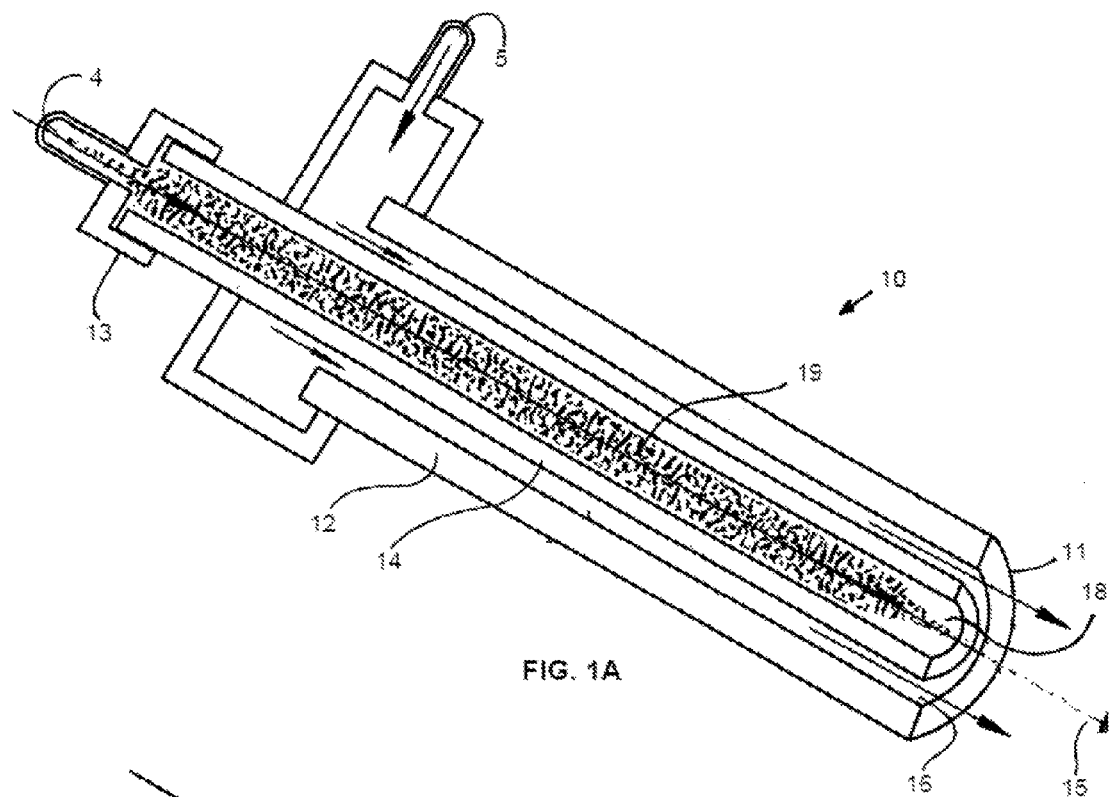
FIG. 1A. illustrates a cross-sectional view of a micro-channel nebulizing nozzle in accordance with an aspect of the present disclosure.

FIG. 7A illustrates the effect of alpha- and gamma-tocopherol on pulmonary gas exchange evaluated by measuring the $PaO_2/FiO_2$ ratio.

FIG. 7B illustrates the effect of alpha- and gamma-tocopherol on changes in lung lymph flow over time.

FIG. 7C illustrates the effect of alpha- and gamma-tocopherol as delivered via the nebulizers of the present disclosure on the pulmonary vascular permeability of a shunt fraction of animals tested, as evaluated by measuring the pulmonary shunt fraction (Qs/Qt) over time.

FIG. 7D illustrates the effect of formulations administered in accordance with the present disclosure on peak airway pressures over time.

FIG. 8 illustrates nebulized fatty acid droplets generated using systems and methods of the present disclosure, impacted on a counting slide.

FIG. 9 illustrates the exemplary gamma-tocopherol concentration in lung tissue.

FIG. 10A illustrates the effect of gamma-tocopherol (γ-T) nebulization on $PaO_2/FiO_2$.

FIG. 10B illustrates the effect of gamma-tocopherol (γ-T) nebulization on pulmonary shunt fractions.

FIG. 11 illustrates the effect of γ-T nebulization on lung lymph flow (pulmonary transvascular fluid flux).

FIG. 12A illustrates the effect of γ-T nebulization on lung wet-to-dry ratio.

FIG. 12B illustrates the effect of γ-T nebulization on airway obstructions.

FIGS. 13A-13B illustrate the effect of γ-tocopherol (γ-T) nebulization on malondialdehyde (MDA) level (A) and 3-nitrotyrosine level (B) in lung tissue.

FIGS. 14A-14B illustrate the effect of γ-tocopherol (T) nebulization on poly(ADP-ribose) polymerase activity in lung tissue.

FIG. 15A illustrates the effect of γ-tocopherol (γ-T) nebulization on IL-8.

FIG. 15B illustrates the effect of γ-tocopherol (γ-T) on mRNA in lung tissue.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "therapeutically effective amount", as used herein, the dose administered to an animal, such as a mammal, in particular a human, should be sufficient to prevent the targeted disease or disorder, e.g., cancer, delay its onset, slow its progression, or treat the disease or disorder (e.g., reverse or negate the condition). One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

"Biological active agent", as used herein, refers to any amino acid, peptide, protein, or antibody, natural or synthetic, which exhibits a therapeutically useful effect. Such biologically active agents may include recombinant proteins, enzymes, peptoids, or PNAs, as well as combinations of such agents.

The phrase "pharmaceutically acceptable" or "pharmacologically-acceptable" refers to compositions that do not produce an allergic or similar unexpected reaction when administered to a human or animal in a medical or veterinary setting.

The compositions of the present invention may be prepared for pharmaceutical administration by methods and with excipients generally known in the art, such as described in *Remington's Pharmaceutical Sciences* [Troy, David B., Ed.; Lippincott, Williams and Wilkins; 21st Edition, (2005)].

"Treating" or "treatment" as used herein covers the treatment of the disease or condition of interest, e.g., tissue injury, in a mammal, preferably a human, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "water-insoluble" encompasses the terms sparingly water-soluble, slightly or very slightly water-soluble, as well as practically or totally water-insoluble compounds [see, *Remington: The Science and Practice of Pharmacy*, vol. I, 194-195 (Gennaro, ed., 1995)]. As used herein, a compound is water-insoluble for the purposes of this invention if it requires at least 30 parts solvent (e.g., water or saline) to dissolve one part solute (Id.). In accordance with the present disclosure, the term "water-insoluble" also encompasses oil- or lipid-soluble, as well as substantially oil- or lipid soluble.

As used herein, the term "tocopherol" includes all such natural and synthetic tocopherol or Vitamin E compounds having the general structure as shown below, including all 10 isomers (five tocopherols (α-, β-, γ-, δ-, $\zeta_1$-) and five tocotrienols (α/$\zeta_1$-, (β/ε-, γ-, δ-, η-), as well as combinations thereof, including but not limited to α-tocopherol (alpha tocopherol)(2,5,7,8-tetramethyl-2-(4',8',12'-trimethyldecyl)-6-chromanole), β-tocopherol (beta-tocopherol), γ-tocopherol (gamma tocopherol), δ-tocopherol (delta tocopherol), and $\zeta_2$-tocopherol, as well as the d, l and dl [also referred to equivalently as the (+), (−), and (±) forms] enantiomers, prodrugs, esters, solvates, and/or polymorphs thereof, or mixtures of any of these compounds. These can be represented generally by the structure (I) below,

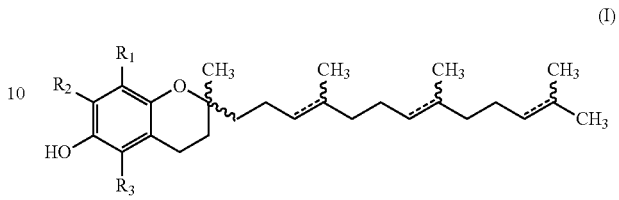

(I)

wherein, $R_1$, $R_2$ and $R_3$ may each alternatively be selected from hydrogen, alkyl, alkenyl, alkynyl, aryl, heteroaryl, aralkyl, and heteroaralkyl moieties, any of which can be unsubstituted or substituted with one or more of the same or different substituents, which are typically selected from —X, —R', =O, —OR', —SR', =S, —NR'R', —NR'R'R'$^+$, =NR', —CX$_3$, —CN, —OCN, —SCN, —NCO, —NCS, —NO, —NO$_2$, =N$_2$, —N$_3$, —S(O)$_2$OH$^-$, —S(O)$_2$OH, —S(O)$_2$R', —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR)NR'R', where each X is independently a halogen (F, Cl, Br, or I, preferably F or Cl) and each R' is independently hydrogen, alkyl, alkenyl, or alkynyl; wherein the wavy line, "〰", represents that the stereochemistry at this point may be in the form of the E- or Z-isomer; and "=====" represents that the carbon-carbon bond may be a single or double (olefinic) bond.

While practical size limits for the various substituent groups will be apparent to those skilled in the art, generally preferred are the alkyl, alkenyl, alkynyl, aryl, heteroaryl, aralkyl, and heteroaralkyl moieties containing up to about 40 carbon atoms, more preferably up to about 20 carbon atoms and most preferably up to about 10 carbon atoms.

As to any of the above groups that contain one or more substituents, it is understood, of course, that such groups do not contain any substitution or substitution patterns which are sterically impractical and/or synthetically non-feasible. In addition, the compounds of this invention include all stereochemical isomers and mixtures thereof arising from the substitution of these compounds.

Except as otherwise specifically provided or clear from the context, the term "compounds" of the invention should be construed as including the "pharmaceutically acceptable salts" thereof (which expression has been eliminated in certain instances for the sake of brevity).

The term "gamma-tocopherol" or "γ-tocopherol", as used herein, refers to 2,7,8-trimethyl-(4,8,12-trimethyltridecyl)chroman-6-ol, alternately and equally acceptably referred to as d-gamma-tocopherol, RRR-gamma-tocopherol, 2R,4'R,8'R-gamma-tocopherol, gamma-TOH, gamma-T and gamma-TH, and having the CAS registry number [54-28-4].

As used herein, the term "vitamin" refers to those compounds which are considered to be nutrients required for essential metabolic reactions within the body, and which are capable of acting both as catalysts and participants in chemical reactions within the body of mammals [Kutsky, R. J. *Handbook of Vitamins and Hormones*. Van Nostrand Reinhold, New York (1973); Kirk-Othmer, *Encyclopedia of Chemical Technology*, Third Edition, John Wiley and Sons, NY, Vol. 24:104 (1984)].

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in *Remington's Pharmaceutical Sciences* [Troy, David B., Ed.; Lippincott, Williams and Wilkins; 21st Edition, (2005)].

The terms "patient" and "subject", as used herein, are used interchangeably and refer generally to a mammal, and more particularly to human, ape, monkey, rat, pig, dog, rabbit, cat, cow, horse, mouse, sheep and goat. In accordance with this definition, lung surfaces or membranes described and referenced in accordance with this disclosure refer to those of a mammal, preferably a human or an animal test subject, such as a sheep.

The term "particle size" or "droplet size" is used in the context of the present disclosure to refer to the average diameter of particles, e.g., drug, lipid vesicles, in a suspension, and is defined herein as the "Mass Median Aerodynamic Diameter" (MMAD) which is referenced from an equivalent aqueous solution with a density of 1.0 g/ml. As the fluid density decreases the real droplet diameter/volume increases and conversely. Lung deposition of a particle or droplet is primarily dependent on the MMAD of the individual particle or droplet.

The term "spray dry" refers to a nebulization method that allows for the evaporation of a solvent in part of the nebulized formulation that results in a smaller droplet after a time when a portion of the droplet has evaporated. Within the context of this disclosure spray drying is an essential part of the operation of handheld inhalers as well as the operation of pharmaceutical manufacturing methods and column injection in analytical chemistry application especially in gas chromatography.

The term "droplet" (or a tiny drop) is an individual particle from a fine spray of liquid that was nebulized into an aerosol.

"Insufflation" as used herein refers to blowing or inhaling a medicinal powder, solution or formulation into the lungs of a patient.

The term "hygroscopic" generally refers herein to a condition whereby a nebulized droplet composition absorbs water from the humidity in the droplet air stream and causes the droplet to expand and grow causing the MMAD to increase in size.

The term "drug" as used in conjunction with the present disclosure means any compound which is biologically active, e.g., exhibits or is capable of exhibiting a therapeutic or prophylactic effect in vivo, or a biological effect in vitro.

DETAILED DESCRIPTION

One or more illustrative embodiments incorporating the invention disclosed herein are presented below. Not all features of an actual implementation are described or shown in this application for the sake of clarity. It is understood that in the development of an actual embodiment incorporating the present invention, numerous implementation-specific decisions must be made to achieve the developer's goals, such as compliance with system-related, business-related, government-related and other constraints, which vary by implementation and from time to time. While a developer's efforts might be complex and time-consuming, such efforts would be, nevertheless, a routine undertaking for those of ordinary skill the art having benefit of this disclosure.

In general terms, Applicants have created nebulizer assemblies, nebulizer fluid nozzle assemblies, and methods of using such assemblies to deliver aerosols comprising one or more water-insoluble or oil-soluble drugs to the pulmonary region of a patient, for the purpose of delivering a therapeutically effective amount of the drug to the pulmonary region so as to treat a disease or disorder of the pulmonary system.

I. Nebulizer Assembly and Design

Turning now to the figures, FIG. 1A provides a nebulizer 10 in accordance with an aspect of the present disclosure. Nebulizer fluid nozzle assembly 10 comprises an outer gas-delivery tube 12 and an inner microtube 14, each of which are concentrically configured and positioned along a central axis 15, and each having a free end at the proximal end 11 of the assembly 10. Intermediate between the outer gas-delivery tube 12 and the inner microtube 14 is an annular intermediate space, which serves to convey the nebulizing carrier gas via gas entry port 5 through the nebulizer needle from the distal to the proximal end, whereupon it acts to nebulize the liquid within inner microtube 14 into an aerosol having an aerosolized particle size ranging from about 1 mm to about 10 mm. In accordance with the present disclosure, the particle size may be controlled by the spatial relationship of tubes 12 and 14 to each other, and the flow rate of the carrier gas. In typical operation, generally speaking, drug emulsion 19 enters the inner microtube 14 of nebulizing assembly 10 via port 4 at the distal end 13, is propelled down the fluid microchannel 18 via an appropriate gas, and is aerosolized into particles of the desired size at the proximal end 11 of the assembly. Appropriate gases for use in nebulization in accordance with the present disclosure include oxygen, oxygen mixtures, nitrogen, argon, helium, and purified air, as well as combinations of these gases in various proportions (e.g., 70% oxygen, 30% nitrogen). While the outer tube 12 and the inner microtube 14 are illustrated to be substantially cylindrical in shape, those of skill in the art will appreciate that they can also be of any appropriate shape, providing such shape provides the same advantageous flow rates and particle sizes as the illustrated arrangement. Additionally, while the nebulizer 10 is illustrated to comprise inner and outer tubes which are substantially blunt at the proximal end 11 of the assembly, it is equally acceptable for either outer tube 12, inner microtube 14, or both to have an outer lip comprising an annular bevel (not shown), the angle of such a bevel ranging from about 5° to about 88°.

Figures 2A, 2B:
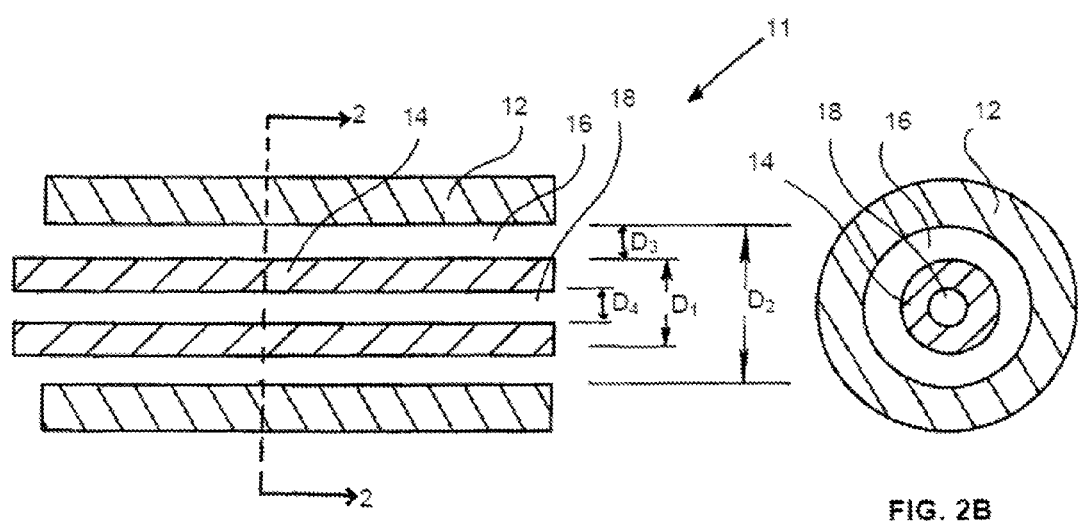
FIG. 2A illustrates a schematic side view of a portion of a nebulizer in accordance with an aspect of the present disclosure.
FIG. 2B illustrates a cross-sectional schematic view of the nebulizer of FIG. 2A, taken along line 2-2.

FIG. 2A illustrates a cross-sectional view of the proximal end 11 of nebulizer fluid nozzle assembly 10. As is apparent therein, the spacing between the outer surface of inner-microtube 14 and the interior surface of outer gas-delivery tube 12 has a diameter $D_3$, and this has a value proportional to the outer diameter $D_1$ of inner-microtube 14. The intermediate air space 16 between the two tubes 12 and 14 may generally be described to be the free air opening value, the value of which is the internal diameter of the outer gas-delivery tube, $D_2$, minus the total outside diameter of the inner microchannel delivery tube, $D_1$. In accordance with aspects of the present disclosure, the outer gas delivery tube 12 has an inner diameter $D_2$ ranging from about 0.01 inches to about 0.05 inches, and the inner microchannel delivery tube 14 has an outer diameter ranging from about 0.01 inches to about 0.04 inches. The value of the intermediate air space between the two tubes ranges from about 0.000009 in$^2$ to about 0.001 in$^2$, and more preferably from about 0.00000259 in$^2$ to about 0.001 in$^2$.

In accordance with further aspects of this disclosure, the nebulizing nozzle 11 preferably has an air volume to nebulized droplet volume ratio less than about 60,000:1, and more preferably an air volume to nebulized droplet volume ratio less than about 15,000:1.

The micro-channel nebulizer assemblies described herein are ideally suited for delivery of aerosols of formulation compositions comprising oil, bound water, or emulsion formulations via nebulization in single or multi-phase water-in-oil or oil-in-water droplets formation. Accordingly, the nebulizer assemblies described herein, such as nozzle assembly 10, are capable of generating aerosol droplets having a particle size ranging from about 2 µm to about 20 µm, preferably from about 2 µm to about 12 µm, and more preferably from about 5 µm to about 10 µm. Such aerosol droplet particle sizes include about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, and about 20 µm, as well as ranges between any two of these values, such as from about 4 µm to about 11 µm.

Figure 3:
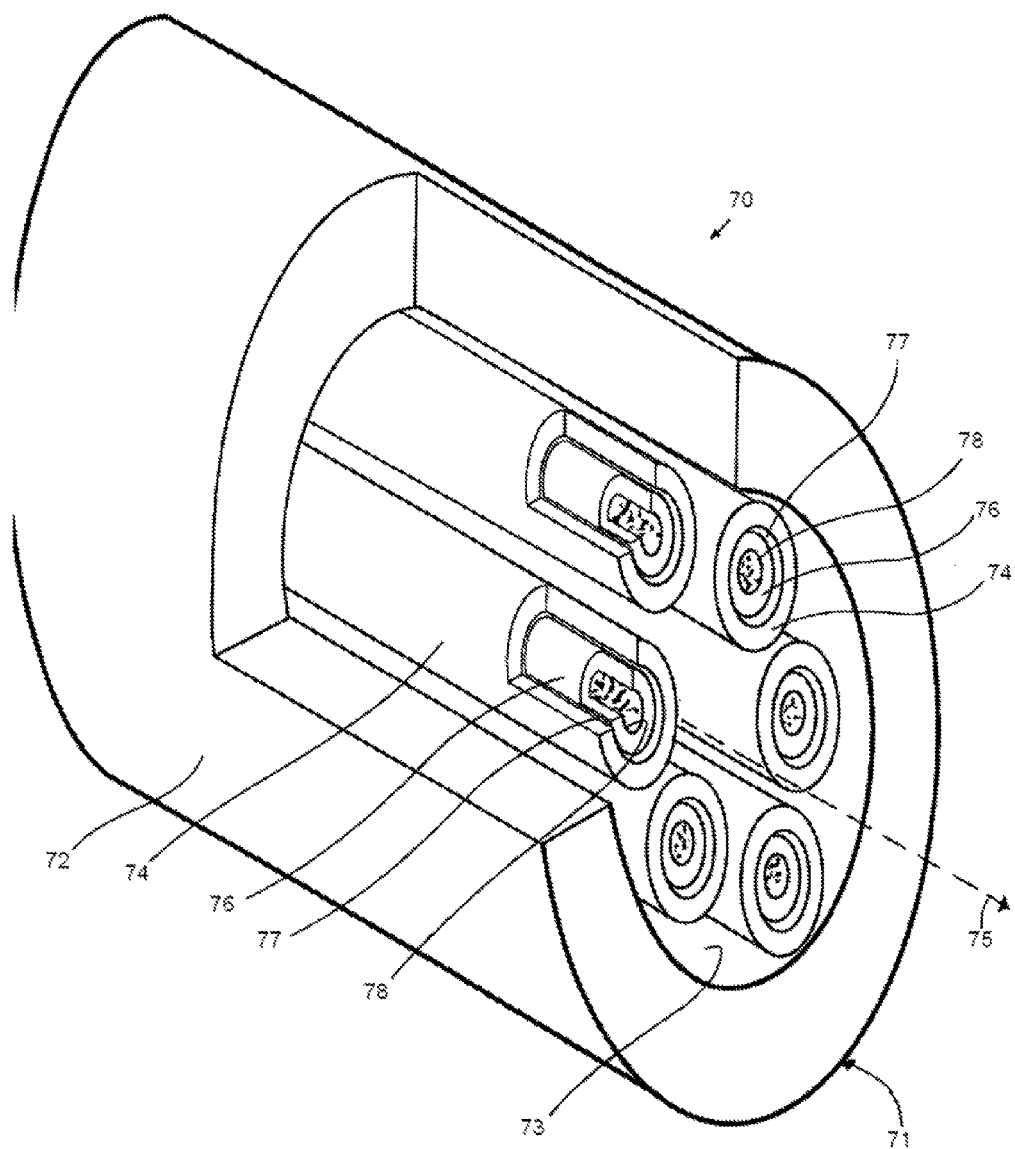
FIG. 3 illustrates a multiple nebulizer nozzle configuration, in accordance with an aspect of the present disclosure.

An alternative aspect of the present disclosure is illustrated in FIG. 3, wherein the proximal end 71 of nebulizing nozzle 70 is shown. In accordance with this aspect, nebulizing nozzle 70 comprises a plurality of individual micro-channel nozzles 74a-74f within a larger mass air channel/annular intermediate space 73 within outer air-delivery tube 72. As shown therein, the plurality of individual micro-channel nozzles 74 is preferably arranged around a central, longitudinal axis 75 extending through outer tube 72. The plurality of individual micro-channel nozzles 74 can range from about 2 to about 12 nozzles, including 3, 4, 5, 6, 7, 8, 9, 10, 11 and 12 individual nozzles.

Nebulizing nozzles and assemblies, in accordance with the present disclosure, may be made from any number of appropriate materials, including but not limited to metals of any appropriate gauge, including stainless steel, metal alloys, coated metals, and polymeric materials, both natural and synthetic, as well as co-polymers, homo-polymers, and ter-polymers of such polymeric materials. Such polymeric materials may include polyethylenes, polyurethanes, polyacrylates, polystyrenes, polymethacrylates, amino-based polymers, cellulosic-based polymers, phenolic-based polymers, and combinations thereof. Coatings suitable for use with the materials for manufacture of the nebulizers and nebulizing assemblies described herein include both natural and synthetic coating materials, and are optionally included on the assemblies so as to enhance the flow rates, protect the outer surface of the materials, or both.

Figure 4:
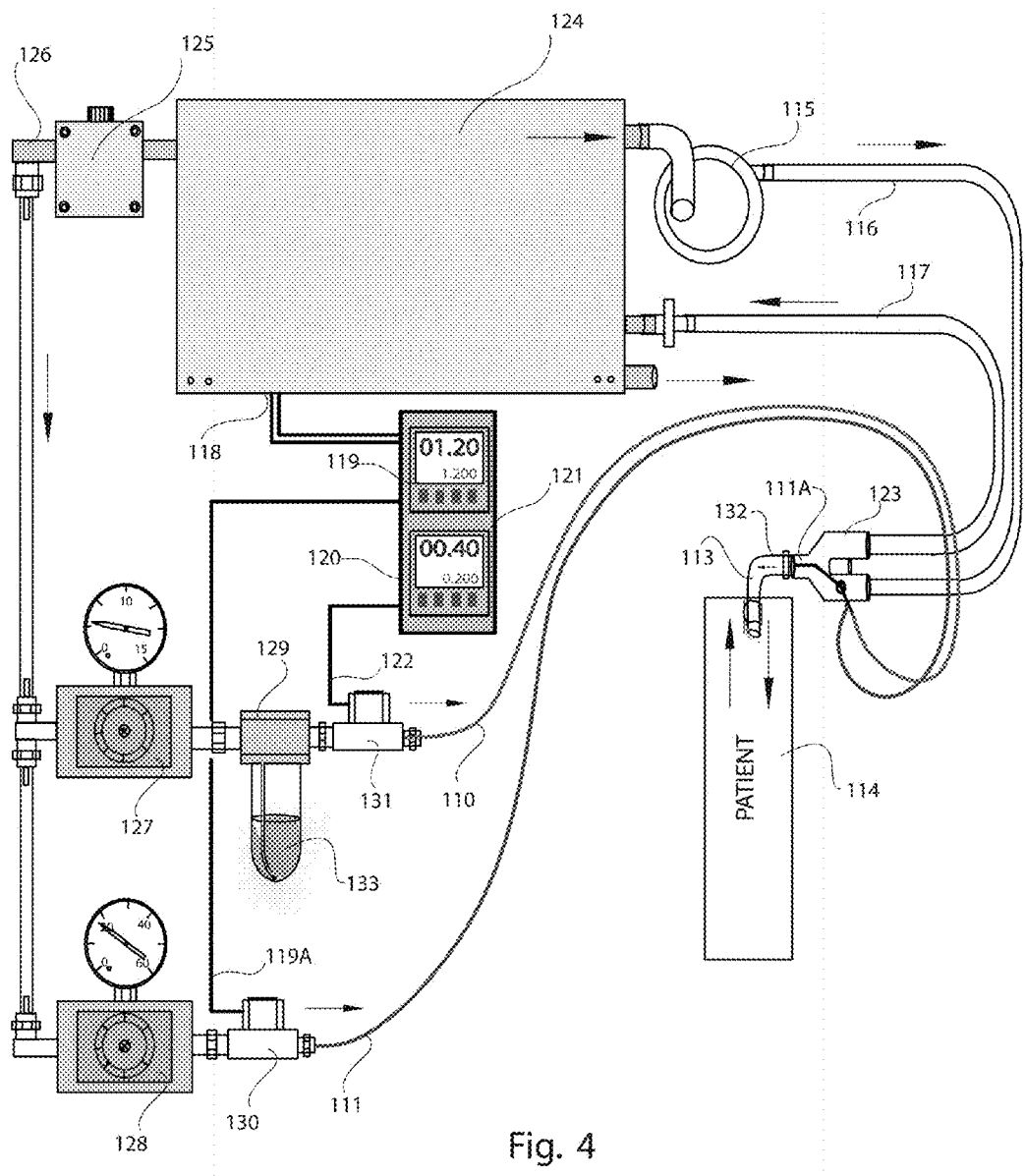
FIG. 4 illustrates a schematic view of a nebulizing system of the present disclosure for use in association with a mechanical ventilator.

Turning to FIG. 4, another aspect of the present disclosure is illustrated generally therein. In the embodiment shown in FIG. 4, a nebulizer system in accordance with the present disclosure may be adapted to work in conjunction with a mechanical ventilator 124 and has been configured to synchronize the cyclic nebulization of drug droplet aerosol mist generation at the nebulizing nozzle 111A and the injection of that drug mist at the beginning of the inspiration cycle of the ventilator and inject the drug aerosol mist directly into the ventilator circuit at the endotracheal tube or tracheal tube 132, and directly into the pulmonary region of the patient 114 via air tube 113. This configuration reduces material loss (e.g., aerosol drug loss) in the ventilator circuit tubing.

The nebulizer nozzle with a "pulse jet" cycle operation in accordance with the present disclosure is configured using the ventilator breath cycle signal output 118 signaling the nebulizer controller 121, having cycle timers 119 and 120. The nebulization of the drug 133 in a oil-based solution in accordance with aspects of the present disclosure and contained within aspirator 129 is commenced at the leading edge of the inspiration cycle and operates for a short period of time at the beginning of inspiration. The output of the nebulizer is synchronized with the inspiration start trigger generated by the existing electronic control outputs of the ventilator. With continued reference to FIG. 4, the ventilator electronic output signal 118 then signals cycle timers 119 and 120 that control electric solenoid valves on the air supply 130 and fluid supply 131 to the nebulizer nozzle 111A, respectively. The nebulization process is substantially instantaneous and independent of the tidal volume inspiration flow volume. The nebulized particles are then injected directly into the ventilator air stream 113 ahead of the bulk of the inspired tidal volume. The output of the nebulizing nozzle 111A may be connected directly into the end of the ventilator tubing "Y" 123 at the ET tube connector. The existing ventilator $O_2$ mixer 125 output may be tapped via connection 126 to provide the nebulizer atomizing gas supply, thus providing nebulizer gas at the same $O_2$ concentration as the ventilator inspired oxygen concentration ($FiO_2$). The nebulizer cycle time, about 1.2 seconds, for the air flow is slightly longer than the fluid flow cycle time, which is about 0.4 seconds. The fluid flow may be delayed about 0.2 seconds from the start of the cycle and ends before the end of the air flow. This dual cycle clears the nozzle with air so the nozzle does not drip. Total drug volume nebulized and delivered with each breath is a function of the fluid cycle duration fluid viscosity/fluid micro-channel size and the number of individual nebulizing nozzles.

The devices described and illustrated in FIG. 4 may be readily manufactured from existing technologies and electronic control configurations. The system uses existing signal generations from the various mechanical ventilation devices as the controller for the nebulizing device. The entire device simply adapts with the existing mechanical ventilating equipment.

Figure 5:
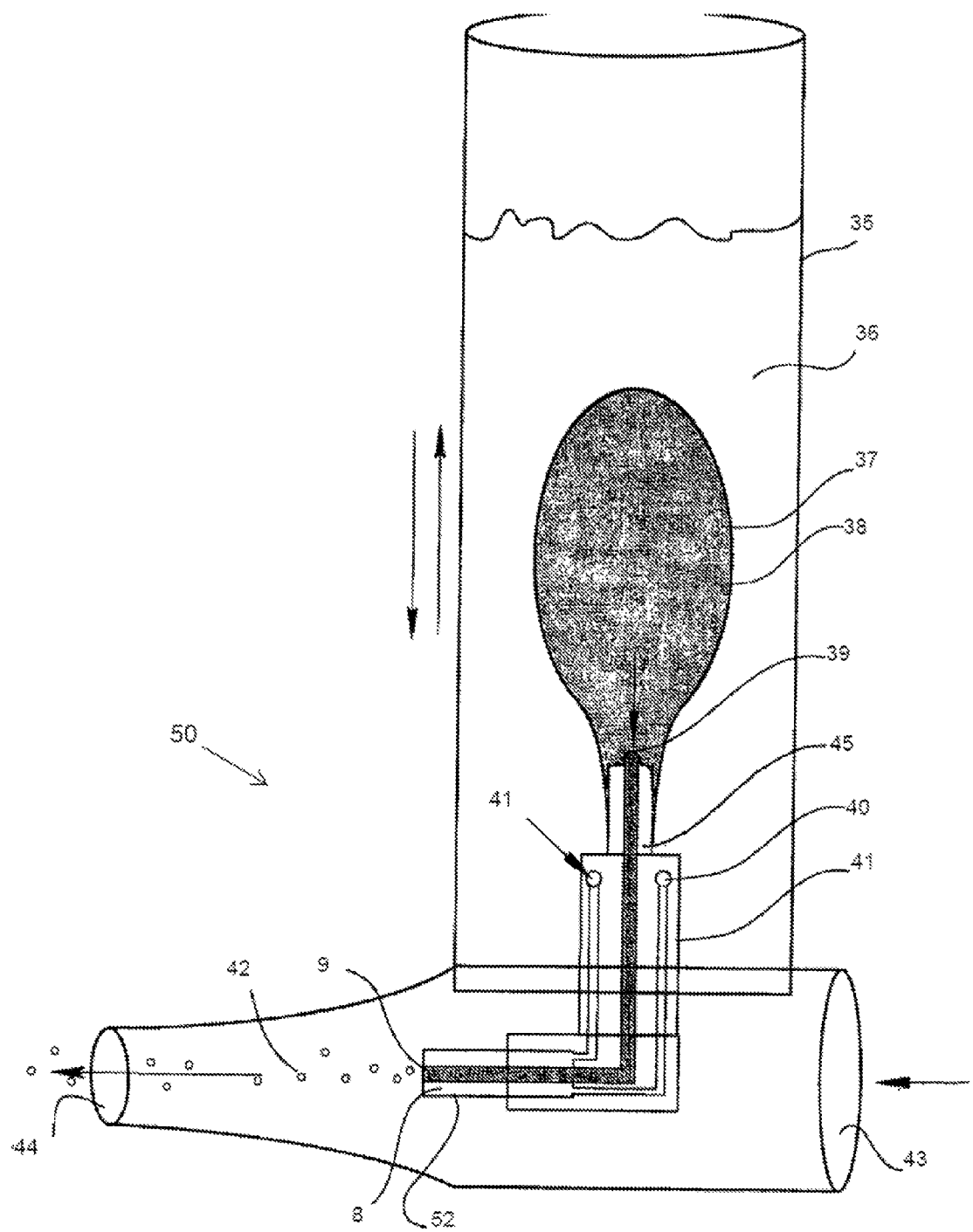
FIG. 5 illustrates a hand-held micro-channel nebulizing system in accordance with an aspect of the present disclosure.

In a further aspect of the present disclosure, a portable handheld nebulizing or inhaler device 50 is illustrated generally in FIG. 5, comprising a lower equalization chamber portion 43 and an upper pressure vessel portion 35, wherein the inhaler device 50 is capable of delivering metered doses of a medicament to a patient. In this arrangement, the medicinal formulation 38 comprising the medicament, such as described in more detail below, is retained within a bladder 37, separated from the propellant gas 36 contained within a pressure vessel 35. In accordance with this structural relationship, the medicinal composition within bladder 37 is not emulsified with the propellant gas 36, thus allowing many different propellant gases to be used in this configuration including those gasses that may be difficult or impossible to solubilize with the drug formulation. Bladder 37 is attached to stem 45 by an appropriate attachment means, including mechanical attachment means such as a clip, chemical attachment means such as medically-acceptable glues and adhesives, and combinations thereof. The drug formulation flow and gas flow is actuated mechanically. Ports 39, 40 in the actuating valve assembly 41 allow the drug composition 38 and the liquefied gas 36 to enter into the valve assembly 41 and on to the nebulizing nozzle 52. Valve assembly 41 acts to not only transfer the drug composition from the bladder 37 to the nebulizing nozzle 52, but also acts to connect pressure vessel 35 with lower equalization chamber 43. The pressurized drug composition flows to the end of the micro-fluid channel 9 and then is disrupted into aerosol mist 42 by the expanding propellant gas. In one aspect of the present disclosure, it is preferable to use a liquefied propellant gas, such as fluorinated hydrocarbon, in this configuration in order to provide enough gas volume for multiple actuations and also to adapt the gas vessel for a lower operating pressure. In accordance with another aspect of the present disclosure, it is preferable to use a non-liquified gas as the propellant gas, such as carbon dioxide, nitrogen, or nitrous oxide. Preferably, in accordance with this aspect, the gas is nitrogen gas, owing to its odorless and tasteless characteristics, and its substantial insolubility in product formulations.

In yet another aspect of the present disclosure, the formulations and devices described herein can provide for medicinal droplets that do not substantially evaporate. As such, a mist of persistent and size stable droplets containing medicine can be generated into a large vessel. In general, droplets in the 2-5 µm are well known to be the optimum size for pulmonary drug delivery and are well known to stay suspended in air with only minor movement of air currents within the vessel. Importantly, in this embodiment, an environment of medicinal droplets is produced in a space and remains suspended and persist as a stable aerosol in the air within the environment until inhaled. The method described would be suitable for passive inhaled drug delivery for one or more persons. More particularly, the embodiment would provide for drug delivery for many persons as in a mass casualty situation where a medicinal nebulizer could be shared with one or more persons. This embodiment would be useful to minimize equipment and personnel for mass inhalation pulmonary drug delivery.

Still, in yet another embodiment, the devices and methods described herein may be useful in industrial applications where the generation of an aerosol from a viscose fluid or emulsion is required. These applications shall include pharmaceutical manufacture, oil micro-droplet lubrication and fuel injection.

II. Nebulizing Mask Adaptations

Figures 6A, 6B:
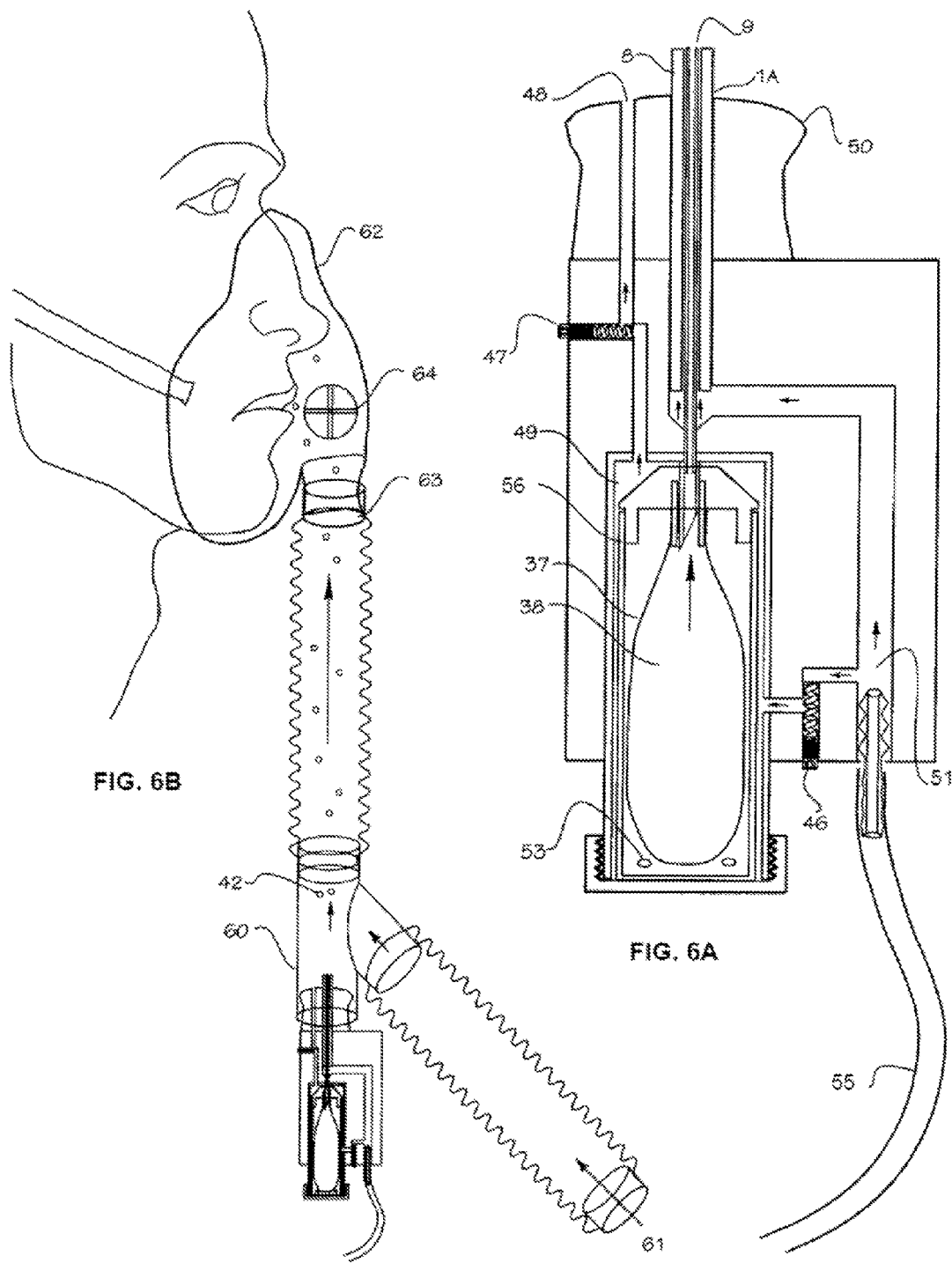
FIG. 6A illustrates a micro-channel nebulizer configured to operate continuously using any standard air/oxygen source commonly available for use in respiratory therapy, for use in association with aspects of this disclosure.

FIG. 6B illustrates an exemplary manner in which the device of FIG. 6A may be adapted to a semi-closed passive breathing circuit.
Figure 7A:
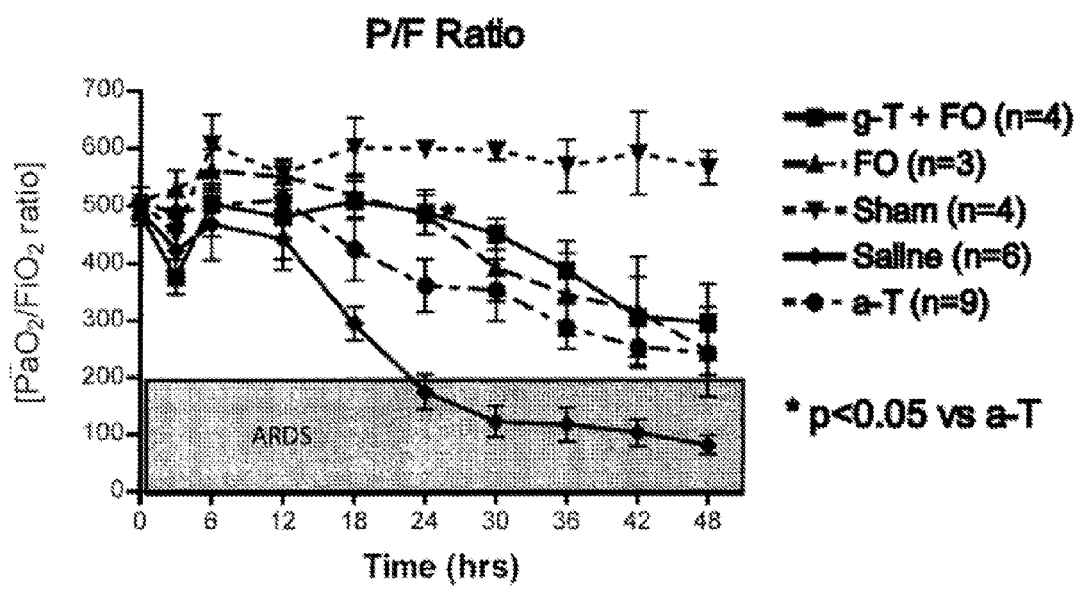
Figure 7B:
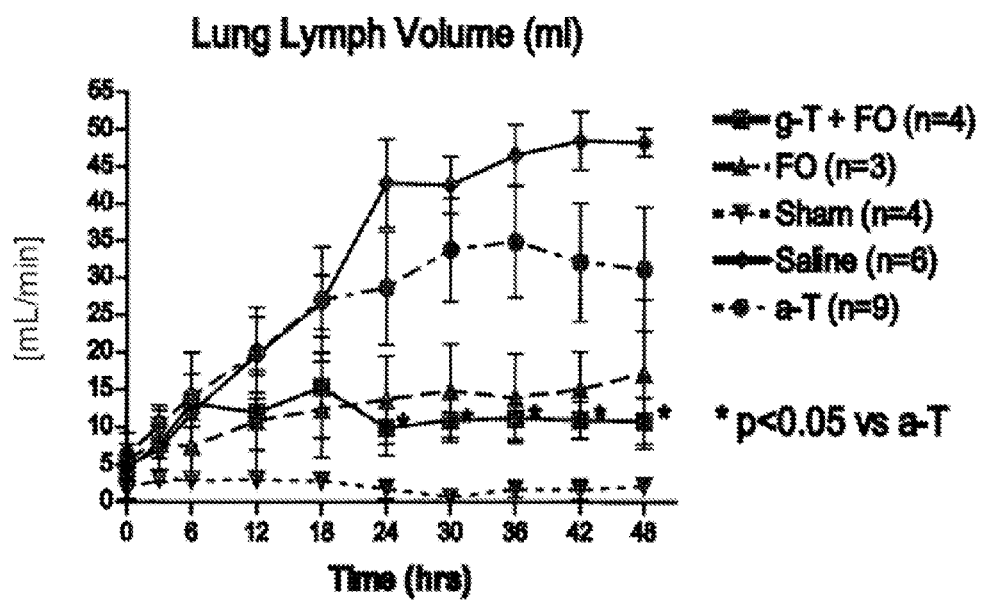
Figure 7C:
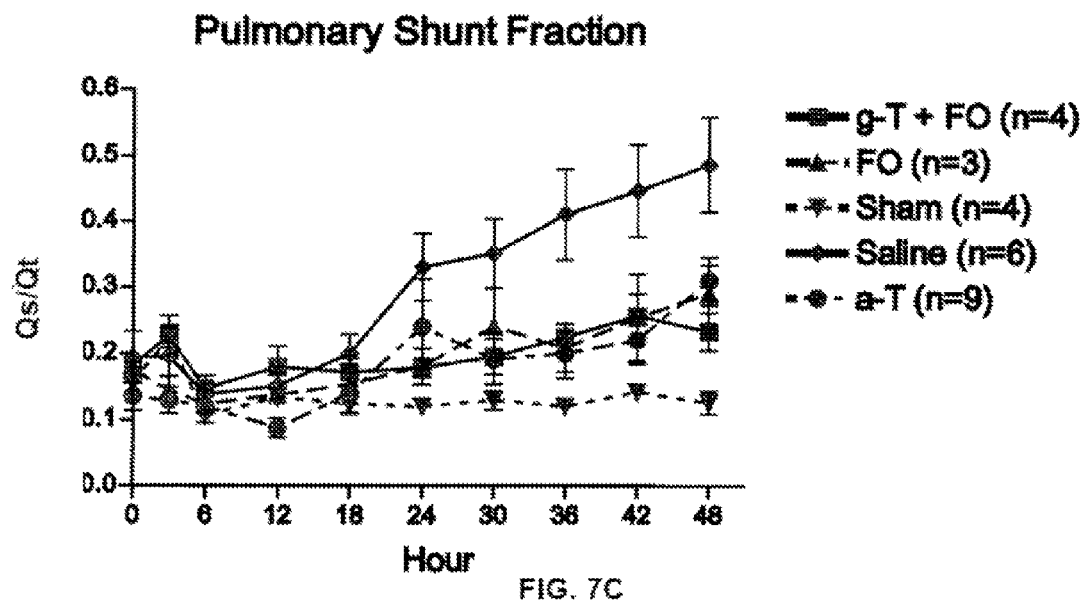
Figure 7D:
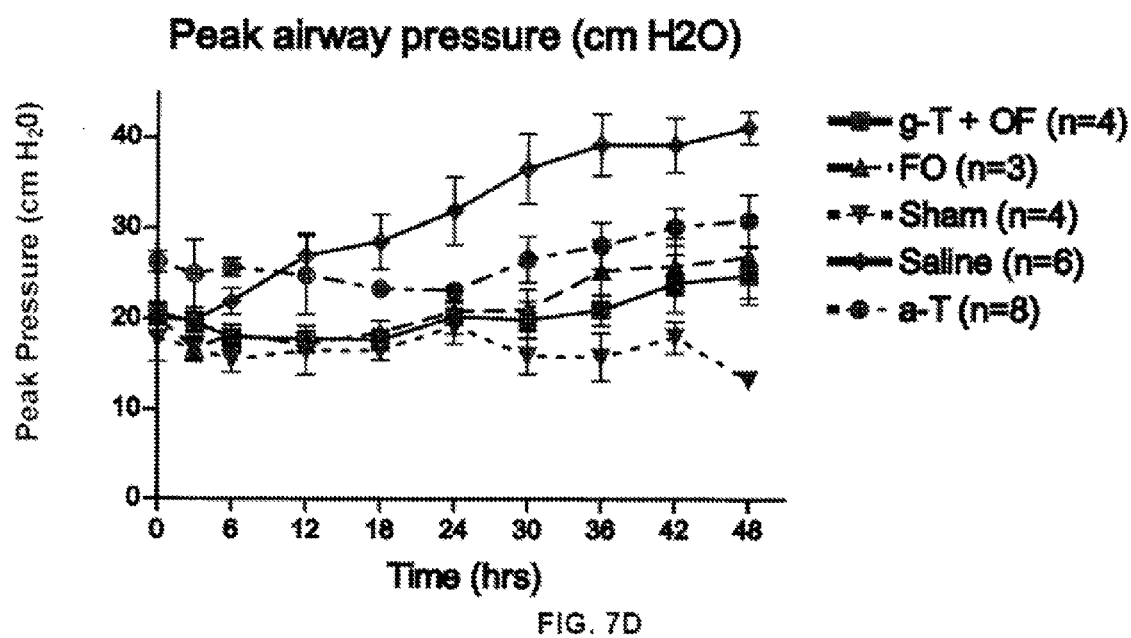

In accordance with further aspects of the present disclosure, and as illustrated in FIG. 6A and FIG. 6B, the micro-channel nebulizer systems described above may be adapted for continuous or semi-continuous nebulization and delivery of inspirable droplets via a semi-closed face mask breathing circuit 62. The drug is contained in a flexible membrane within a pressurized housing, which allows for the nebulizer to operate in various positions unaffected by gravity. Humidified air is provided by a separate standard mask humidifier which is existing equipment for face mask delivery of oxygen. The mask and lipid nebulizer is intended to be adaptable to existing equipment.

There are certain instances wherein it is desirable to provide medicines by nebulization and subsequent inhalation by a spontaneously breathing person. In this application, the face mask may be coupled to a nebulizer drug delivery system for delivering an aerosolized drug through the face mask, such that medicines are continuously nebulized into a space that holds the medicinal droplets suspended in a contained inspirable air flow which is in proximity to the mouth and nose of the person. The nebulizer continuously generates droplets into the air volume in a tube connected to a close fitting mask coving the mouth and nose of the person. As the person inhales the medicine/air mixture, the medicine enters the lungs via the mouth and nose. On exhale, a valve on the mask opens and allows the exhaled air to flow out of the system.

FIG. 6A generally illustrates a micro-channel nebulizer configured to operate continuously using any standard (e.g., 50 psi) air/oxygen source commonly available for use in respiratory therapy, for use in association with this aspect of the disclosure. A micro-channel nebulizing nozzle 1A may be pressed into a plastic block containing air channels and a pressurized medicament chamber 49. Air/oxygen is supplied through a hose 55 connected to the ports of the air channel 51. Air is allowed to flow through the channel 51 and on to the micro-channel air delivery tube 8. A portion of the supplied air is regulated by a spring loaded flow valve 46 and allowed to flow into and pressurize the medicine reservoir chamber 49 containing a medicine reservoir assembly 56. Another spring loaded blow-off valve 47 regulates the pressure in medicament reservoir 49. Excess pressure, as regulated by blow-off valve 47, is vented through a port 48. The pressure in the reservoir exerts pressure through ports 53 on the medicament bladder 37 and forces the medicine 38 in the bladder 37 into the micro-channel liquid delivery tube 9.

FIG. 6B illustrates an exemplary manner in which the continuous nebulizing device in FIG. 6A may be adapted to a semi-closed passive breathing circuit. As illustrated therein, a face mask 62 is included, wherein the face mask is contoured to cover the nose and mouth of a patient. Humidified air 61 and nebulized medicine is combined in a "Y" adapter 60. The humidified air/medicinal mist is then fed into the face mask through port 63. The person inhales the medicine/air mixture during the course of normal respiration, and then exhales. The person's exhaled breath may then be vented through one or more one-way valves 64 on mask 62, allowing the exhaled breath to exit the breathing circuit without inhibiting the flow of nebulized medicine.

III. Formulation of Water-Insoluble Drugs

Compositions comprise water-insoluble or substantially water-insoluble drugs or biologically active substances, as well as oil-soluble or lipid-soluble drugs and biologically active substances, in combination with one or more lipids or fatty acids, including naturally-occurring fats and oils. In accordance with one aspect of the present disclosure, the compositions can comprise a water-insoluble or substantially water-insoluble drug or biologically active substance and one or more fatty acids. In a further aspect, the compositions can comprise a water-insoluble or substantially water-insoluble drug or biologically active substance, one or more fatty acids, and one or more surfactants. In yet another aspect, the compositions suitable for use with the nebulizer assemblies of the present disclosure can comprise a water-insoluble or substantially water-insoluble drug or biologically active substance, water, and at least one gelling agent.

The compositions, according to the invention, may be comprised of a drug itself or any mixture of a biologically active substance with a solvent, and oil, a gelling agent, a carrier or adjuvant, emulsifier, one or more different drugs, polymers, excipients, coatings and combinations thereof. In essence, the drug(s) or substances can be combined with any combination of pharmaceutically acceptable components to be delivered to the cellular surfaces within the pulmonary system by the method described herein, e.g., pulmonary drug delivery. The drug(s) does not have to be dissolved in a drug delivery medium solvent but can be suspended or emulsified in a solvent or medium. The delivery medium can take the form of an aqueous mixture, oil, or an organic liquid. The delivery media solution can also comprise microspheres or nanospheres of biologically active substances.

The compounds useful in the formulations and therapeutically-useful compositions of the present invention can be used in the form of pharmaceutically acceptable salts derived from inorganic or organic acids. The term "pharmaceutically acceptable salt" as used herein is meant to refer to those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zunch, Switzerland: 2002). The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, flimarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final preparation, formulation, or purification of the therapeutically-useful compounds, substantially water-insoluble compounds described for use in aspects of this disclosure by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Pharmaceutically acceptable salts of compounds which may be used in formulations and systems described herein may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids can also be made.

The formulations described for use herein may conveniently be presented in unit dosage form and may be prepared by any of the methods well known in the art of pharmacy. All methods include the step of bringing into association one or more of the compounds described herein, or a pharmaceutically acceptable salt or solvate thereof ("active ingredient"), with a carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

The compound or a pharmaceutically acceptable ester, salt, solvate or prodrug thereof, such as a pharmaceutically acceptable ester, salt, solvate, or prodrug of alpha-, beta-, or gamma-tocopherol, can be mixed with other active materials that do not impair the desired action, or with materials that supplement the desired action, including other drugs against inflammatory disease or lung injury.

As recited above, the present invention uses (1) a novel nebulizing nozzle configuration that requires limited energy from a compressed gas to cause droplet nebulization from a mass fluid into droplets of a suitable size; and (2) a drug carrier(s) that is based on essential fatty acid oils, lipids, gelled aqueous solutions, emulsions, or combinations thereof that are harmlessly absorbed by the lung tissues and are metabolized or expired.

Water-insoluble, substantially water-insoluble drugs, or sparingly water soluble drugs suitable for use in the medicament compositions of the present disclosure include, but are not limited to, vitamins, antioxidants, anti-bronchitus agents, anti-pneumonia agents, pulmonary anti-cancer agents, anti-anginal agents, antihypertensive agents, and combinations thereof. In accordance with one aspect of the present disclosure, the preferred drug is a vitamin or a combination of two or more vitamins. Suitable vitamins for use herein include but are not limited to Vitamin A, Vitamin B (including Vitamin $B_{12}$), Vitamin C, Vitamin D, Vitamin E, Vitamin K3 (menadione; 1,4-dehydro-1,4-dioxo-2-methyl-naphthalene, MNQ), retinol, riboflavin, niacin, ascorbic acid, β-carotene, and Coenzyme Q, including various derivatives of Coenzyme Q having various isoprenoid side chains, including but not limited to QH, $QH_2$, $Q_3$ and $Q_{10}$.

In accordance with a further aspect of the present disclosure, the formulation composition suitable for nebulization using the assemblies described herein comprises Vitamin E, also known as tocopherol, or a derivative, metabolite, ester, hydrate, solvate, prodrug, or polymorph thereof. Tocopherols suitable for use in the compositions herein include all those tocopherols within the range of natural and synthetic compounds known by the generic term Vitamin E. In accordance with one aspect of the present disclosure, the tocopherol may be selected from the group consisting of alpha-tocopherols, beta-tocopherols, gamma-tocopherols, and delta tocopherols, as well as combinations thereof. Tocopherols occur in a number of isomeric forms, the D and DL forms being most widely available, all of which are suitable for use herein. In accordance with one aspect of the present disclosure, the tocopherols are preferably gamma-tocopherols.

Tocopherols suitable for use in accordance with these aspects of the present disclosure may be obtained from plants, such as by extracted from plants using known procedures, or prepared synthetically using known organic synthetic methods, all of which are in accordance with the present disclosure. Additionally, and as suggested above, any of the forms or isomers of tocopherols and their derivatives, eg. esters may be used according to the present invention. Thus for example, gamma-tocopherol can be used as such, or in the form of its esters such as gamma-tocopherol acetate, linoleate, nicotinate or hemi succinate-ester, many of which are available commercially or through known synthetic routes.

In accordance with further aspects and embodiments of the present disclosure, the compositions may comprise antianginal and/or antihypertensive drugs or biologically active agents which are insoluble or substantially insoluble in water, or exhibit poor water solubility (e.g., less than about 5 mg/mL). Compounds of these types suitable for use herein include inhibitors of cAMP (3',5'-cyclic adenosine monophosphate), cGMP (3',5'-cyclic guanosine monophosphate), inhibitors of cGMP-specific phosphodiesterase type IV (PDE IV), inhibitors of c-GMP-specific phosphodiesterase type V (PDE V), drugs that may exhibit anti-anginal effects, including drugs which exhibit therapeutic effects on angina pectoris, and compounds which can enhance the natriuretic effect of atrial natriuretic peptide (ANP). Suitable examples of such drugs include but are not limited to atenolol, amlodipine, diltiazem, eplerenone, naphthyriclin-4-one derivatives, griseolic acid, dihydrodesoxygriseolic acid, derivatives of griseolic acid and dihydrodesoxygriseolic acid, angiotensin converting enzyme inhibitors, todalafil, vardenafil, ranolazine [see, Tafreshi, M. J., et al., *Ann. Pharmacother.*, Vol. 40(4): pp. 689-693 (2006)], sildenafil, sildenafil citrate (Viagra®; Pfizer, Inc., New York), N-desmethyl sildenafil, and T-1032 (methyl-2-(4-aminophenyl)-1,2-dihydro-1-oxo-7-(2-pyridinylmethoxy)-4-(3,4,5-trimethoxyphenyl)-3-isoquionoline carboxylate sulfate; see: Noto, T., et al., *J. Pharm. Exp. Ther.*, Vol. 294(3): pp. 870-875 (2000)], as well as derivatives, solvates, prodrugs, and polymorphs thereof. In accordance with one aspect of this embodiment, the drug is sildenafil. Such drugs may be used in a therapeutically effective amount ranging from about 1 mg/kg/d to about 1,000 mg/kg/d, as well as therapeutically effective amounts within this range.

"Naturally-occurring fats and oils" as used herein refers to the glyceryl esters of fatty acids (i.e., triglycerides) normally found in animal or plant tissues, including those which have been hydrogenated to reduce or eliminate unsaturation. Naturally occurring fats and oils include vegetable oils such as linseed oil, soybean oil, sunflower seed oil, corn oil, sesame oil, olive oil, castor oil, coconut oil, palm oil, peanut oil, jojoba oil, neem oil, and *macadamia* nut oil.

Selected naturally-occurring fats and oils suitable for use in formulations of the present disclosure include, but are not limited to, the following compounds: Adansonla Digitata Oil; Apricot (*Prunus armeniaca*) Kernel Oil; Argania Spinosa Oil; Argemone Mexicana Oil; Avocado (*Persea gratissima*) Oil; Babassu (*Orbignya olelfera*) Oil; Balm Mint (*Melissa officinalis*) Seed Oil; Bitter Almond (*Prunus amygdalus amara*) Oil; Bitter Chemy (*Prunus cerasus*) Oil; Black Currant (*Ribes nigrum*) Oil; Borage (*Borago officinalis*) Seed Oil; Brazil (*Bertholletia excelsa*) Nut Oil; Burdock (*Arctium lappa*) Seed Oil; Butter; C12-18 Acid Triglyceride; Calophyllum Tacamahaca Oil; Camellia Kissi Oil; Camellia Oleifera Seed Oil; Canola Oil; Caprylic/Capric/Liuric Triglyceride; Caprylic/Capric/Linoleic Triglyceride; Caprylic/Capric/Myristic/Stearic Triglyceride; Caprylic/Capric/Stearic Triglyceride; Caprylic/Capric Triglyceride; Caraway (*Carum carvi*) Seed Oil; Carrot (*Daucus Carota Sativa*) Oil; Cashew (*Anacardium occidentale*) Nut Oil; Castor Oil Benzoate; Castor (*Ricinus communis*) Oil; Cephalins; Chaulmoogra (*Taraktogenos kurzii*) Oil, Chia (*Salvia hispanica*) Oil; Cocoa (*Theobrama cocao*) Butter; Coconut (*Cocos nucifera*) Oil; Cod Liver Oil; Coffee (*Coffea arabica*) Oil; Corn (*Zea mays*) Germ Oil; Corn (*Zea mays*) Oil; Cottonseed (*Gossypium*) Oil; C10-18 Triglycerides; Cucumber (*Cucumis sativus*) Oil; Dog Rose (*Rosa canina*) Hips Oil; Egg Oil; Emu Oil; Epoxidized Soybean Oil; Evening Primrose (*Oenothera biennis*) Oil; Fish Liver Oil; Gevuina Avellana Oil; Glyceryl Triacetyl Hydroxystearate; Glyceryl Triacetyl Ricinoleate; Glycolipids; Glycosphingolipids; Goat Butter; Grape (*Vitis vinifera*) Seed Oil; Hazel (*Croylus americana*) Nut Oil; Hazel (*Corylus aveilana*) Nut Oil; Human Placental Lipids; Hybrid Safflower (*Carthamus tinctorius*) Oil; Hybrid Sunflower (*Helianthus annuus*) Seed Oil; Hydrogenated Canola Oil; Hydrogenated Castor Oil; Hydrogenated Castor Oil Laurate; Hydrogenated Castor Oil Triisostearate; Hydrogenated Coconut Oil; Hydrogenated Cottonseed Oil; Hydrogenated C12-18 Triglycerides; Hydrogenated Fish Oil; Hydrogenated Lard; Hydrogenated Menhaden Oil; Hydrogenated Milk Lipids; Hydrogenated Mink Oil; Hydrogenated Olive Oil; Hydrogenated Orange Roughy Oil; Hydrogenated Palm Kernel Oil; Hydrogenated Palm Oil; Hydrogenated Peanut Oil; Hydrogenated Rapeseed Oil; Hydrogenated Shark Liver Oil; Hydrogenated Soybean Oil; Hydrogenated Tallow; Hydrogenated Vegetable Oil; Isatis Tinctoria Oil; Job's Tears (*Coix Lacryma-Jobi*) Oil; Jojoba Oil; Kiwi (*Actinidia chinensis*) Seed Oil; Kukui (*Aleurites Moluccana*) Nut Oil; Lard; Lauric/Palmitic/Oleic Triglyceride; Linseed (*Linum usitatissiumum*) Oil; Lupin (*Lupinus albus*) Oil; Macadamia Nut Oil; *Macadamia Ternifolia* Seed Oil; *Macadamia Integrifolia* Seed Oil; Maleated Soybean Oil; Mango (*Mangifera indica*) Seed Oil; Marmot Oil; Meadowfoam (*Limnanthes fragra alba*) Seed Oil; Menhaden Oil; Milk Lipids; Mink Oil; Moringa Pterygosperma Oil; Mortierella Oil; Musk Rose (*Rosa moschata*) Seed Oil; Neatsfoot Oil; Neem (*Melia azadirachta*) Seed Oil; Oat (*Avena sativa*) Kernel Oil; Oleic/Linoleic Triglyceride; Oleic/Palmitic/Lauric/Myristic/Linoleic Triglyceride; Oleostearine; Olive (*Olea europaea*) Husk Oil; Olive (*Olea europaea*) Oil; Omental Lipdis; Orange Roughy Oil; Ostrich Oil; Oxidized Corn Oil; Palm (*Elaeis guineensis*) Kernel Oil; Palm (*Elaeis guineensis*) Oil; Passionflower (*Passiflora edulis*) Oil; Peach (*Prunus persica*) Kernel Oil; Peanut (*Arachis hypogaea*) Oil; Pecan (*Caiya illinoensis*) Oil; Pengawar Djambi (*Cibotium barometz*) Oil; Phospholipids; Pistachio (*Pistacia vera*) Nut Oil; Placental Lipids; Poppy (*Papaver orientale*) Oil; Pumpkin (*Cucurbita pepo*) Seed Oil; Quinoa (*Chenopodium Quinoa*) Oil; Rapeseed (*Brassica campestris*) Oil; Rice (*Oryza sativa*) Bran Oil; Rice (*Oryza sativa*) Germ Oil; Safflower (*Carthamus tinctorius*) Oil; Salmon Oil; Sandalwood (*Santalum album*) Seed Oil; Seabuchthorn (*Hippophae rhamnoides*) Oil; Sesame (*Sesamum indicum*) Oil; Shark Liver Oil; Shea Butter (*Butyrospermum parkii*); Silk Worm Lipids; Skin Lipids; Soybean (*Glycine soja*) Oil; Soybean Lipid; Sphingolipids; Sunflower (*Helianthus annuus*) Seed Oil; Sweet Almond (*Prunus amygdalus dulcis*) Oil; Sweet Chemy (*Prunus avium*) Pit Oil; Tali Oil; Tallow; Tea Tree (*Melaleuca alternifolia*) Oil; Telphairia Pedata Oil; Tomato (*Solanum lycopersicum*) Oil; Triarachidin; Tiibehenin; Tricaprin; Tricaprylin; Trichodesma Zeylanicum Oil; Trierucin; Triheptanoin; Triheptylundecanoin; Trihydroxymethoxystearin; Trihydroxystearin; Triisononanoin; Triisopalmitin; Triisostearin; Trilaurin; Trilinolein; Trilinolenin; Trimyristin; Trioctanoin; Triolein; Tripalmitin; Tripalmitolein; Triricinolein; Trisebacin; Tristearin; Triundecanoin; Tuna Oil; Vegetable Oil; Walnut (*Juglans regia*) Oil; Wheat Bran Lipids; Wheat (*Triticum vulgare*) Germ Oil, and combinations of such fatty acid oils. In accordance with one preferred aspect of this embodiment, the formulation composition comprises Linseed Oil, which is also known as flaxseed oil, as well as fatty acids found therein, including but not limited to linolenic acid (LA), linoleic acid, oleic acid, stearic acid, palmitic acid, alpha-linolenic acid (LNA), and gamma-linolenic acid (GLA), any of which may be saturated or unsaturated as appropriate. In accordance with further aspects of the present disclosure, the formulations may also comprise hylauronic acid in an amount suitable to minimize water from transpiring across the droplets formed by the nebulizer.

Tocopherol, and in particular gamma tocopherol, compositions of the present invention may further optionally comprise preservatives. As used herein, the term "preservative" is intended to mean a compound used to prevent the growth of microorganisms. Such preservatives may be used in the tocopherol and gamma tocopherol pharmaceutical compositions described herein at typical concentrations in accordance with current pharmaceutical practices as described. [see: *The United States Pharmacopeia—National Formulary,* 29th Edition, (2006) Rockville, Md.; and, *Remington's Pharmaceutical Sciences*, 21st Edition, Troy, D B, Ed. Lippincott, Williams and Wilkins; (2005)]. Exemplary preservatives which may be used with the compositions and systems of the present disclosure include but are not limited to antifungal and antimicrobial preservatives, such as benzoic acid, hydroxy benzoate and its derivatives, butylparaben, ethylparaben, methylparaben, propylparaben, sodium benzoate, benzalkonium chloride, benzethonium chloride, benzyl alcohol, cetylpyridinium chloride, chlorobutanol, phenol, phenylethyl alcohol, phenylmercuric nitrate and thimerosal; and antioxidants, such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, and sodium metabisulfite, as well as combinations of two or more of the these preservatives.

Tocopherol and gamma tocopherol pharmaceutical compositions and formulations of the present invention may further comprise one or more pH modifying agents (buffering agents), in order to maintain the pH of the composition in the desired range, e.g., from a pH of from about 3.5 to about 8. pH modifying agents suitable for use herein, include, but are not limited to, inorganic salts, alkali earth and/or alkali rare earth hydroxides (e.g., NaOH, KOH, or CsOH); carbonate or bicarbonate of any appropriate alkali or alkali rare earth metal (e.g., $Na_2CO_3$, $K_2CO_3$, $NaHCO_3$, and $KHCO_3$); phosphates, such as calcium hydrogen phosphate, potassium metaphosphate, and potassium phosphate monobasic; inorganic acids such as hydrochloric acid (HCl), and organic acids such as acetic acid, citric acid, succinic acid, fumaric acid, malic acid, maleic acid, glutaric acid or lactic acid, as well as combinations thereof, any of which may be water-soluble or water-insoluble, anhydrous or hydrated (e.g., dehydrate or semihydrate), as appropriate.

Others components which may be included in the therapeutically useful compositions of the present disclosure include but are not limited to binding materials (e.g., block polymers, natural and synthetic rubber, polyacrylates, polyurethanes, silicones and styrene-butadiene copolymers); colorants, including but not limited to FD & C yellow #6, FD & C red #40, FD & C blue #2, and FD & C violet #1, as well as any other appropriate dye or combination of dyes; and, UV inhibitors, to inhibit UV decomposition or isomerization of the therapeutic compositions.

Other pharmaceutically acceptable formulation excipients may also be used in accordance with the formulation compositions described and disclosed herein, including but not limited to coatings, stabilizers, emulsifiers, and the like, such as those described in "*The Handbook of Pharmaceutical Manufacturing Formulations*" [Niazi, S. K., CRC Press (2004)]. Additionally, and in accordance with aspects of the present disclosure, one or more surface active agents (surfactants) may be added to the formulation compositions as appropriate. Although not required, incorporation of a compatible surfactant can improve the stability of the instant respiratory dispersions, increase pulmonary deposition and facilitate the preparation of the suspension. Moreover, by altering the components, the density of the particle or structural matrix may be adjusted to approximate the density of the surrounding medium and further stabilize the dispersion. Any suitable surface active agent (surfactant) may be used in the context of the present invention, provided that the surfactant is preferably physiologically acceptable. Physiologically acceptable surfactants are generally known in the art and include various detergents and phospholipids, as discussed in more detail below. In accordance with one aspect, it is preferred that the surfactant is a phospholipid including, but not limited to, an extract of a natural surfactant such as any number of known pulmonary surfactants, including bovine- and calf-lung surfactant extracts, an egg phospholipid, a vegetable oil phospholipid such as a soybean phospholipid, or phosphatidylcholine. Preferably, in accordance with aspects of the present disclosure, the surfactant suitable for use with the therapeutic compositions of the present disclosure is an extract of a natural surfactant, an egg phospholipid, or combinations thereof. More preferably, the compositions may any one or more of a number of biocompatible materials as surfactants, such as surfactants comprising phospholipids.

In a broad sense, surfactants suitable for use in the present invention include any compound or composition that aids in the formation and maintenance of the stabilized respiratory/pulmonary dispersions by forming a layer at the interface between the particles of therapeutic compound (e.g., tocopherol or γ-tocopherol) and the suspension medium. The surfactant may comprise a single compound or any combination of compounds, such as in the case of co-surfactants. In accordance with certain aspects of the present disclosure, depending upon the specific therapeutic composition or formulation, preferred surfactants include but are not limited to those surfactants that are substantially insoluble in the medium, nonfluorinated, and selected from the group consisting of saturated and unsaturated lipids, especially those that are obtained or extracted from natural sources, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized therapeutic preparations.

Lipids, including phospholipids, from both natural and synthetic sources are particularly compatible with the present inventions and may be used in varying concentrations to form the particle or structural matrix useful in the final, therapeutic compositions. Generally compatible lipids include those that have a gel to liquid crystal phase transition greater than about 40° C. Preferably, and as described in more detail below, the incorporated lipids are relatively long chain (i.e. $C_{16}$-$C_{22}$) saturated lipids and preferably comprise one or more phospholipids. Exemplary phospholipids useful in the disclosed stabilized preparations of the present invention comprise egg phosphatidylcholine, dilauroylphosphatidylcholine, dioleylphosphatidylcholine, dipalmitoylphosphatidyl-choline, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein. With regard to biologically-compatible surfactants comprising phospholipids, in accordance with certain aspects of the present disclosure, it is preferable that such biologically-compatible surfactants for use with the therapeutic compositions described herein, especially those comprising tocopherol and/or gamma-tocopherol, include those surfactants that are extracts of natural surfactants, in particular pulmonary surfactants, and synthetic synthesized mixtures of pulmonary surfactants in order to mimic natural lung surfactant. Exemplary surfactants suitable for use with the present compositions of tocopherol and gamma-tocopherol include but are not limited to SURVANTA® (beractant, available from the Ross Products Division of Abbott Laboratories), a bovine-lung pulmonary surfactant comprising phospholipids, neutral lipids, fatty acids, and surfactant-associated proteins; SURFAXIN® (lucinactant, available from Discovery Laboratories, Inc.); INFASURF® (calfactant, available from Forest Pharmaceuticals, Inc., St. Louis, Mo.), an extract of natural surfactant from calf lung which includes phospholipids, neutral lipids, and hydrophobic surfactant-asasociated proteins B and C(SP-B and SP-C); CUROSURF® (poractant alpha, available from Chiesi Farmaceutici, S.p.A., Parma, Italy), a non-pyrogenic pulmonary surfactant that is an extract of natural porcine lung comprising polar lipids (mainly phospholipids) and hydrophobic low molecular weight proteins (surfactant associated proteins SP-B and SP-C); and ALVEOFACT® (available from Boehringer Ingelheim Pharma, Ingelheim, Germany), a natural bovine extract/surfactant comprising bovine lung phospholipids; as well as the synthetic pulmonary surfactants EXOSURF®, VENTICUTE®, ADSURF® (Pumactant™), and KL-4, all of which synthetic surfactants comprise the phospholipid dipalmitoylphosphatidylcholine (DPPC).

Compatible nonionic detergents for use in the formulations of the present disclosure comprise, without limitation, sorbitan esters including sorbitan trioleate (SPAN™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents include any of those which can be easily identified using "McCutcheon's Emulsifiers and Detergents" (McPublishing Co., Glen Rock, N.J.) which is incorporated herein in its entirety. Preferred block copolymers include but are not limited to diblock and triblock copolymers of polyoxyethylene and polyoxypropylene, including poloxamer 188 (PLURONIC™ F-68), poloxamer 407 (PLURONIC™ F-127), and poloxamer 338. Ionic surfactants such as sodium sulfosuccinate, and fatty acid soaps may also be utilized. In accordance with certain aspects and embodiments of the present disclosure, the therapeutic compositions described herein may comprise oleic acid or its alkali salt.

Those skilled in the art will further appreciate that, a wide range of surfactants, including those not listed above, may optionally be used in conjunction with the present invention. Moreover, the optimum surfactant, or combination thereof, for a given application can readily be determined by empirical studies that do not require undue experimentation. It will further be appreciated that, the preferred insolubility of any incorporated surfactant in the suspension medium will dramatically decrease the associated surface activity. As such, it is arguable as to whether these materials have surfactant-like character prior to contracting an aqueous bioactive surface (e.g. the aqueous hypophase in the lung).

On a weight to weight basis, the instant formulations and compositions of the therapeutic compositions comprising tocopherols such as gamma-tocopherol may comprise varying levels of surfactant. In this regard, the compositions and formulations described herein which include one or more surfactants will preferably comprise greater than about 0.1%, about 1%, about 5%, about 10%, about 15%, about 18%, or even about 20% w/w % surfactant. In accordance with a further aspect of the present disclosure, the therapeutic compositions and formulations described herein may comprise greater than about 25%, about 30%, about 35%, about 40%, about 45%, or about 50% w/w surfactant. Still other exemplary embodiments of the present disclosure will include therapeutic compositions and formulations as described herein, further comprising one or more surfactants, wherein the surfactant or surfactants are present at greater than about 55%, about 60%, about 65%, about 70%, about 75%, about 80%, about 85%, about 90% or even about 95% w/w.

In certain embodiments, the present invention employs a novel composition comprising one or more lipids associated with at least one drug. A lipid as referred to herein is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid for use with the present disclosure may be naturally occurring or synthetic (i.e., designed or produced by man). However, a lipid is typically a biological substance. Biological lipids are well known in the art, and include for example and without limitation, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

A. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphatidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example and without limitation, vitamin A, coenyzme Q and carotenoids (e.g., lycopene and β-carotene).

B. Charged and Neutral Lipid Compositions

In certain embodiments, a lipid component of a composition in accordance with the present disclosure may be uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 50%, about 55%, about 60%, about 65%, about 70%, about 75%, about 80%, about 85%, about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

C. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") may be obtained from K & K Laboratories (Plainview, N.Y.); cholesterol ("Chol") may be obtained from Calbiochem-Behring; dimyristyl phosphatidylglycerol ("DMPG") and other lipids known to those of skill in the art may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol, allowing for more expedient lipid recovery.

D. Lipid Composition Structures

In one preferred embodiment of the invention, the drugs may be associated with one or more lipids, instead of or in addition to, the fatty-acid. In accordance with this aspect of the disclosure, a drug associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/chimeric polypeptide associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-chimeric polypeptide or Superfect (Qiagen)-chimeric polypeptide complex is also contemplated.

In accordance with certain aspects of the present disclosure, a fatty acid- or lipid-containing composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 90%, about 91%, about 92%, about 93%, about 94%, about 95%, about 96%, about 97%, about 98%, about 99%, about 100%, or any range derivable therein, of a particular lipid, lipid type or fatty acid, in combination with one or more therapeutic components such as a drug, biologic agent, or other therapeutic material disclosed herein or as would be known to one of skill in the art. In a non-limiting example, a lipid composition may comprise about 10% to about 20% neutral lipids, and about 13% to about 84% of a tocopherol such as gamma-tocopherol, and about 1% cholesterol. Thus, it is contemplated that lipid compositions of the present invention may comprise any of the lipids, lipid types or other components in any combination or percentage range.

The compositions according to the present disclosure may also comprise antibiotics as the drug, or in combination with one or more drugs, e.g., in combination with tocopherol. Antibiotics suitable for use according to the invention are selected from the group including but not limited to amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, tetracycline, coxycycline, chloramphenicol, and zithromycin.

Compositions according to the invention may also contain a "gelling agent" in combination with the drug or biologically active agent and lipid. The gelling agent may be selected from the group including but not limited to hydroxyethyl cellulose (HEC), hydroxymethylcellulose (HMC), Natrasol®, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, tyloxapol (a nonionic surfactant oligomer), proteins and sugars.

IV. Therapeutic Treatment

The formulations of water-insoluble and substantially water-insoluble compounds may be used, in combination with the nebulizer systems described herein, in order to administer a therapeutically effective amount of one or more drugs or biological agents as an aerosolized mixture. Preferably, and in accordance with an aspect of the present disclosure, the formulations comprising one or more water-insoluble compounds and a lipid can be administered using a nebulizer as described herein for the treatment of one or more pulmonary diseases. Pulmonary diseases and disorders which may be treatable using the compositions, formulations, methods, and apparatus/systems of the present disclosure include but are not limited to asthma; alpha-1 antitrypsin deficiency (AAT Deficiency); dust-related pulmonary and lung diseases and disorders, including asbestosis; avian flu; bronchitis, including acute bronchitis; bronchiectasis; bronchopulmonary dysplasia (BPD); chronic cough; chronic obstructive pulmonary diseases and disorders; the common cold; chronic obstructive pulmonary disorder (COPD); croup; cystic fibrosis (CF); emphysema; farmer's lung; influenza; hantavirus; rhinitis (hay fever); histoplasmosis; interstitial lung disease; legionellosis (Legionnaire's disease); lung cancer (including both small cell, large cell and mixed small cell/large cell carcinoma); lung damage resultant from inhalation of smoke and heat; inflammation and lung damage resultant from inhalation of chemicals; lymphangioleiomyomatosis (LAM); occupational lung disease; pleurisy; pneumonia; pneumothorax; pulmonary embolus; pulmonary fibrosis; pulmonary hypertension; respiratory distress syndrome; respiratory syncytial virus (RSV); sarcoidosis; severe acute respiratory syndrome (SARS); sleep apnea; and tuberculosis, as well as two or more such diseases or disorders exhibiting themselves simultaneously. In accordance with one embodiment of the present disclosure, the preferred pulmonary disorder to be treated is lung damage resultant from inhalation of heat and smoke. In accordance with a further embodiment of the present disclosure, the pulmonary disorder to be treated is bronchitis.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Comparative Example

Two ultrasound nebulizers, DeVilbiss Ultra-Neb 99 (available from Sunrise Medical, Respiratory Products Div., Somerset, Pa.) and Aeroneb-Pro® (available from Aerogen, Inc., now Nektar Therapeutics, Mountain View, Calif.) and an AirLife™ jet nebulizer (Cardinal Health, Inc., Dublin, Ohio) were selected for testing tocopherol nebulization. The viscose tocopherol preparation (neat tocopherol) would not nebulize with these devices, regardless of their manipulation or air flow adjustment. Tocopherol was then dissolved into an essential fatty acid rich flax seed oil (linseed oil) preparation (comprising a variety of fatty acids, including linolenic acid, linoleic acid, oleic acid, stearic acid, and palmitic acid) at a concentration of 8.3% w/w. This much less viscose mixture was then introduced into the selected nebulizers above and again tested. As before, the tocopherol-fatty acid mixture could not be nebulized using these commercially-available devices. It is apparent from these tests that the existing, commercially available nebulizing apparatus are not designed for, and are largely incapable of, nebulizing viscose liquids into droplets of an appropriate size suitable for pulmonary delivery.

Example 2

Measured Air Flow of Nebulizer Nozzles of the Present Disclosure

Table 1 demonstrates the measured air flow of selected micro-channel nozzle configurations whereby a selected fluid nozzle 14 is surrounded by an air delivery tube 12. Nebulizing air in this example is delivered at 50 psi. The free air space surrounding the fluid delivery tube 14 enclosed by the air delivery tube 12 provides for the calculated "SQ inch Neb Free Air Opening". The actual nebulized air flow rate "Neb Air Flow cc/sec" is related to the free air opening size however, the amount of air flowing through a given free air space is also influenced by the resistance offered by the surfaces of the delivery tubes 14 and 12 in contact with the air and may not be linear in function.

TABLE 1

Approximate Air flow rates with various nozzle combination configurations.

| Config. | Gauge Size Fluid/Air | Fluid O.D. "1 O.D." | Neb Air I.D. "2 I.D." | SQ inch Neb Free Air Opening | *Neb Air Flow cc/sec |
|---|---|---|---|---|---|
| A | 22/16 | .0280 | .0470 | .00111920 | 175 |
| B | 22/18 | .0280 | .0330 | .00023955 | 30 |
| C | 25/16 | .0200 | .0470 | .00142079 | 267 |
| D | 25/18 | .0200 | .0330 | .00054114 | 110 |
| E | 25/20 | .0200 | .0230 | .00001013 | 40 |
| F | 27/16 | .0160 | .0470 | .00153389 | 300 |
| G | 27/18 | .0160 | .0330 | .00065424 | 140 |
| H | 27/20 | .0160 | .0230 | .00021441 | 60 |
| I | 27/22 | .0160 | .0170 | .00000259 | 15 |
| J | 30/16 | .0120 | .0470 | .00162185 | 320 |
| K | 30/18 | .0120 | .0330 | .00074220 | 110 |
| L | 30/20 | .0120 | .0230 | .00030238 | 95 |
| M | 30/22 | .0120 | .0160 | .00008796 | 45 |

*Air pressure at 50 PSI

Figure 1B:
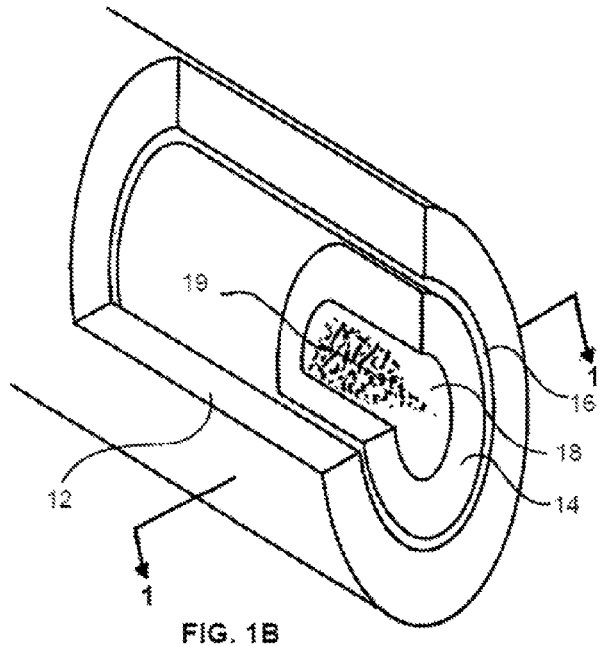
FIG. 1B. illustrates a partial cut-away view of the proximal end of the nebulizing nozzle illustrated in FIG. 1A.
Figure 1C:
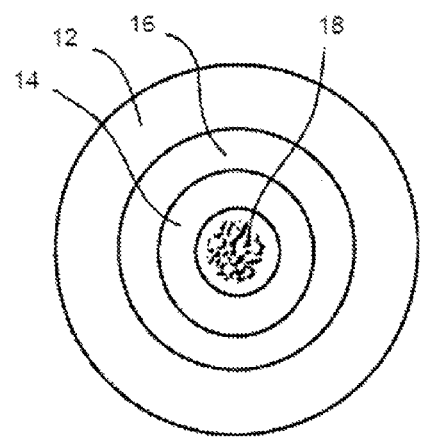
FIG. 1C illustrates an end-view of the proximal end of the nebulizing nozzle of FIG. 1B, taken along line 1-1.

Table 2 demonstrates the fluid delivery rates of various viscosity fluids though various fluid delivery tubes 14 (FIG. 1A-1C) at various fluid pressures. The actual fluid flow rate is related to the delivery tube internal diameter size however, the amount of fluid flowing through a given fluid opening is also influenced by the resistance offered by the surfaces of the delivery tube 14 in contact with the fluid as well as the surface tension of the fluid to be delivered and may not be linear in function. Configurations are based on the nozzle configurations described in Table 1, above.

TABLE 2

Approximate Fluid Flow Rates at Various Fluid Pressures With Various Fluid Nozzles.

| Config. | Fluid Nozzle G Size | Internal diameter | Fluid Pressure PSI | Flow rate 100% ETOH cc/sec | Flow Rate 0.9% Saline cc/sec | Flow Rate Flax Oil cc/sec |
|---|---|---|---|---|---|---|
| A, B | 22 | .0160 | 5 | 0.125 | 0.110 | 0.0034722 |
| A, B | 22 | .0160 | 10 | 0.333 | 0.300 | 0.0073529 |
| A, B | 22 | .0160 | 20 | 0.435 | 0.400 | 0.0195744 |
| A, B | 22 | .0160 | 30 | 1.000 | 0.857 | 0.0241935 |
| C-E | 25 | .0100 | 5 | 0.0233 | 0.0221 | |
| C-E | 25 | .0100 | 10 | 0.050 | 0.0487 | |
| C-E | 25 | .0100 | 20 | 0.111 | 0.1071 | |
| C-E | 25 | .0100 | 30 | 0.200 | 0.1866 | 0.0038265 |
| F-I | 27 | .0080 | 5 | 0.010 | 0.0092 | |
| F-I | 27 | .0080 | 10 | 0.023 | 0.0189 | |
| F-I | 27 | .0080 | 20 | 0.045 | 0.0396 | |
| F-I | 27 | .0080 | 30 | 0.68 | 0.0618 | 0.0023585 |
| J-M | 30 | .0060 | 5 | 0.00336 | 0.003195 | |
| J-M | 30 | .0060 | 10 | 0.00698 | 0.006662 | |
| J-M | 30 | .0060 | 20 | 0.01376 | 0.013102 | |
| J-M | 30 | .0060 | 30 | 0.020027 | 0.019032 | 0.0006527 |

Table 2 demonstrates the measured air flow of selected micro-channel nozzle configurations whereby a selected fluid nozzle 14 is surrounded by an air delivery tube 12. Nebulizing air in this example is delivered at about 50 psi. The free air space 16 surrounding the fluid delivery tube 14 enclosed by the air delivery tube 12 provides for the calculated "SQ inch Neb Free Air Opening". The actual nebulized air flow rate "Neb Air Flow cc/sec" is related to the free air opening size however, the amount of air flowing through a given free air space is also influenced by the resistance offered by the surfaces of the delivery tubes 14 and 12 in contact with the air and may not be linear in function.

Example 3

In this example, and as illustrated in Table 3, the preferred configurations derived from Tables 1 and 2 are demonstrated. This is by way to show the preferred nebulizing air flow rates of the combinations sited but does not limit the arrangements of various combinations of fluid and air tube sizes that achieve the preferred embodiment. The preferred free nebulizing air open area ranges from about 0.000009 to 0.001 square inches. Nebulizing air pressures can be lowered in instances were there is a larger free air opening in order to bring the nebulizing air flow rate into the preferred range of ≥100 cc/second. Nebulizing air pressures, fluid pressures, micro-channel fluid tube size and the viscosity of the fluid to be nebulized are selected from a range of components of fluid delivery tubes 1 and air delivery tubes 2 to achieve the preferred air and fluid flow rates and the nebulized droplet size within the preferred air volume to viscous liquid volume ratio of less than about 60,000:1.

TABLE 3

Preferred Nozzle Configurations

| Config. | Gauge Size Fluid/Air | *Neb Air Flow cc/sec |
|---|---|---|
| B | 22/18 | 30 |
| D | 25/18 | 110 |
| E | 25/20 | 40 |
| H | 27/20 | 60 |
| K | 30/18 | 110 |
| L | 30/20 | 95 |
| M | 30/22 | 45 |

*Air pressure at 50 PSI

Example 4

Animals:

Adult female sheep were cared for in the Investigative Intensive Care Unit at the University of Texas, Galveston Branch. The experimental procedure was approved by the Animal Care and Use Committee of the University of Texas Medical Branch. The National Institutes of Health and American Physiological Society guidelines for animal care were strictly followed. The Investigative Intensive Care unit is accredited by The Association for the Assessment and Accreditation of Laboratory Animal Care International.

Animal Model:

Sheep (30-40 kg) were surgically prepared, as described by Enkhbaatar, P. K., et al. [*Am. J. Physiol. Regul. Inter. Comp. Physiol.*, Vol. 285(2): R366-R372 (2003)]. A Swan-Ganz thermal dilution catheter (model 93A-1317-F, Edwards Critical Care Division, Irvine, Calif.) was inserted through the right external jugular vein for the measurement of the core body temperature to evaluate blood gas and the fluid resuscitations. An arterial catheter was inserted into the right femoral artery (16 gauge, 24 in., Intracath, Becton Dickinson, Sandy, Utah) for the measurement of arterial blood gas. To evaluate changes in lung lymph flow, an efferent lymph vessel from the caudal mediastinal lymph node was cannulated (Silastic catheter 0.025-in ID, 0.047-in OD; Dow Corning, Midland, Mich.) according to a modification of the technique described by Staub and colleagues [Staub, N., et al., *J. Surg. Res.*, Vol. 19, pp. 315-320 (1975); Traber, D., et al., *J. Appl. Physiol.*, Vol. 54, pp. 1167-1171 (1983)]. After a 7-day recovery period, the sheep were deeply anesthetized with halothane and were given a burn (40% total body surface area [TBSA], third degree) and inhalation injury (48 breaths of cotton smoke, <40° C.). After burn/smoke injury, all sheep were placed on a ventilator with positive end-expiratory pressure set to 5 cm $H_2O$ and tidal volume maintained at 15 mL/kg. The latter tidal volume is equal to about 10 ml/kg in humans due to the large dead space of sheep [Melo, V., et al., *Anesthesiology*, Vol. 97, pp. 671-681 (2002)]. All animals were given fluid resuscitation with Ringer's solution strictly according to the Parkland formula (4 mL/kg % TBSA burned/ 24 hr). The experiment was continued for 48 hr.

Animal Grouping:

The animals were randomized into 3 groups as follows: (1) a Vitamin E nebulization group (B&S, Vitamin E, n=6). To achieve the desired particle size, 1 gram mixed tocopherols [1000 mg Decanox™ MTS-90G (94 mg/g alpha tocopherol, 15 mg/g beta-tocopherol, 604 mg/g gamma-tocopherol, 201 mg/g delta tocopherol for a total of 914 mg/g total mixed tocopherols), purchased from Daniels Midland Co., Decatur, Ill.] was added to 11 grams of linseed oil (flax oil) and mixed for 3 hours to make an 8.3% (w/w) solution of tocopherol in linseed oil before starting the nebulization, using a nebulizer as described with the present disclosure. Nebulization was started 1 hour after the combined burn and smoke inhalation injury, and repeated every 12 h. (2) A saline nebulization group (B&S, Saline, n=6): injured and nebulized with 15 mL saline at the same intervals as the vitamin E treatment. (3) A sham group (Sham, n=5): cared for similarly to the other groups, that is, given the same amount of fluid as burned animals, placed on a ventilator, and studied for 48 h but not injured or treated with saline or tocopherol.

Burn and Smoke Inhalation Injury:

The protocol followed was similar to that described in the art [Kimura, R., et al., J. Appl. Physiol., Vol. 64(3): pp. 1107-1113 (1988); Enkhbaatar, P., et al., Am. J. Physiol. Regal. Integr. Comp. Physiol., Vol. 285(2): pp. R366R-372 (2003)]. Briefly, under induction of anesthesia with 10 mg/kg ketamine (Ketalar, Parke-Davis, Morris Plains, N.J.), a tracheotomy was performed, and a cuffed tracheostomy tube (10-mm diameter; Sheiley, Irvine, Calif.) was inserted. Anesthesia was maintained with halothane. Using a Bunsen burner, a third-degree flame burn of 20% of the total body surface area was made on 1 flank of the subject. Thereafter, inhalation injury was induced while the sheep was in the prone position as described previously [id.]. A modified bee smoker was filled with 50 g burning cotton toweling and was connected to the tracheostomy tube via a modified endothoracheal tube containing an indwelling thermistor from a Swan-Ganz catheter. During the insufflation procedures, the temperature of the smoke did not exceed 40° C. The sheep were insufflated with a total of 48 breaths of cotton smoke. After smoke insufflation, another 20% total body surface area, third-degree burn, was made on the contralateral flank.

Resuscitation Protocol:

The protocol for subject resuscitation has been described previously in the art [id.]. Briefly, immediately following the injury, anesthesia was discontinued and the animals were allowed to awaken and were mechanically ventilated with a Servo ventilator (model 900C, Simens-Elena, Solna, Sweden) throughout the next 48 h experimental period. Ventilation was performed with a positive end-expiratory pressure (PEEP) of 5 cm $H_2O$ and a tidal volume of 15 mL/kg. The respiratory rate was set to maintain normocapnia. For the first 3 h post-injury, all animals received an inspired oxygen concentration ($FiO_2$) of 100% to expedite the removal of carbon monoxide (CO); thereafter, the $FiO_2$ was adjusted to maintain the arterial oxygen saturation to be greater than 90%. These respiratory settings allowed rapid carboxyhemoglobin clearance after smoke inhalation.

During the experiment, fluid resuscitation was performed with Ringer lactate solution following the formula (4 mL/% burn surface area/kg body weight for the first 24 h and 2 mL/% burned surface area/kg body weight per day for the next 48 hours). During this experimental period, the animals were allowed free access to food, but not to water, to allow accurate determination of fluid balance.

Concurrent cutaneous burn and smoke inhalation (B&S) injuries have gross evidence of lung oxidant injury. Additionally, inflammatory blood cells, neutrophil granulocytes, infiltrate the lung tissues causing edema, swelling and additional tissue damage from products of the inflammatory cells. Neutrophil infiltrate is an integral part of the formation or obstructive airway cast formation following inhalation injury. Obstructive airway casts is the major cause of pulmonary obstruction following inhalation injury. Pulmonary obstruction reduces the flow of air in and out of the lung and is the primary cause of death following inhalation injury. Therefore, we hypothesized that direct lung insufflation by nebulization of gamma-tocopherol (γ-T), a potent reactive oxygen and nitrogen scavenger, would attenuate this injury by reducing oxidative stress. Additionally, flax seed oil as used in the present examples is made up of about 69% short chain essential fatty acids, which also have been shown to exhibit anti-inflammatory properties, and was used as a carrier for an 8.3% solution of mixed tocopherols.

Acute lung injury was induced in adult female sheep by smoke inhalation (48 breaths of cotton smoke, <40° C.) with concurrent 40% TBSA 3rd degree cutaneous burn under deep anesthesia. Sheep (35.4±1.0 kg) were divided into 4 groups: 1) sham (not injured, nebulized flax oil (FO)) n=4; 2) saline (injured, nebulized saline, n=6); 3) FO (injured, nebulized FO, n=4); and 4) gamma-tocopherol+FO (injured, nebulized FO-gT, n=4). Insufflation by nebulization was started 1 h post-injury and 22 ml FO with or without g-T (mixed natural tocopherols, 528 mg/48 h) was continuously delivered into the pulmonary system for 48 hours using the subject lipid nebulization system using the control system as shown in FIG. 4 with a nebulizing nozzle in accordance with FIG. 1A-1C, and configured as described in Table 1, Configuration H, of Example 1.

Cardiopulmonary variables were unchanged in sham animals receiving flax seed oil over 48 hours and flax seed oil with 8.3% mixed tocopherols (FIG. 7A). Combined burn and smoke inhalation injury caused severe pulmonary dysfunction evidenced by deteriorated pulmonary gas exchange (FIG. 7A), increased pulmonary vascular permeability (FIGS. 7B and 7C), and increased ventilatory pressures (FIG. 7D) were observed. These changes were associated with decreased lung gT levels. FO nebulization significantly improved the pathological changes seen in the saline group (FIGS. 7A-D). Gamma-tocopherol addition further improved pulmonary function (FIGS. 6A-D) along with 100-fold elevation in the lung γ-T concentrations (18.0±7.6 vs. 0.017±0.005 in saline group).

Pulmonary administration by nebulization of flax seed oil did not interfere with gas exchange or other pulmonary function when administered at a rate of ≤0.5 cc per hour in uninjured sham animals. All (6/6) saline nebulized control animals (FIG. 7A) deteriorated into respiratory distress (ARDS defined as a blood $PO_2$ ratio to inspired $O_2$ concentration of ≤200; $PO_2$:$FiO_2$ or P/F Ratio≤200) within 24 hours of the combined burn and smoke inhalation injury. None (0/4) of the animals receiving nebulized flax oil with 8.3% mixed tocopherols administered at 0.3 to 0.5 cc/hour deteriorated into ARDS. All physiological parameters (FIGS. 7A-D) were significantly improved in the insufflated flax oil/tocopherol group as compared with the saline nebulization group.

Histological examination of lung and burn wound tissues was performed during animal sacrifice necropsy at 48 hours post injury. Profound inflammatory cell infiltrate of neutrophils was noted in the B&S Saline control group in both the lung and burn wound tissues. Neutrophil infiltrate was noted in airway casts following smoke inhalation injury in the B&S Saline control group. A marked reduction in inflammatory cell neutrophil infiltrate was noted in the flax (FO) group and the gamma-tocopherol+flax (FO-gT) group. These observations along with the physiological measurements demonstrate that inspired flax (FO) and the gamma-tocopherol+flax (FO-gT) reduces the local and systemic inflammatory response following a smoke inhalation injury.

Example 5

Comparison of Lipid Carrier Compositions

Two medicinal lipid compositions were prepared, and compared using the techniques described in the examples above. The first composition comprised tocopherol and flax seed oil as a carrier, wherein the flax seed oil comprised at least five (5) fatty acids, as shown in Table 4, below. The second, comparative composition comprised tocopherol and a "special" purified fatty-acid mixture (available from Nu-Chek Prep, Inc., Elysin, Minn.) having a high (greater than about 50 wt. %) linolenic acid content. The comparative compositions are shown in Table 4. Initial tests seem to suggest that the use of the "special" mixture with the high omega-3-linolenic acid content may be even more advantageously beneficial in reducing inflammatory response in the lungs of a patient, following lung injury.

TABLE 4

Comparison of standard Flax Seed oil and Purified "Special" Oil from Nu-Chek Prep., Inc.

| Oil | Linolenic Acid (C-18) | Linoleic Acid (C-18) | Oleic Acid (C-18) | Stearic Acid (C-18) | Palmitic Acid (C-16) |
|---|---|---|---|---|---|
| Flax Seed Oil (Linseed) | 47 wt. % | 24 wt. % | 19 wt. % | 3 wt. % | 6 wt. % |
| Purified "Special" Oil | 68 wt. % | 29 wt. % | 3 wt. % | — | — |

Example 6

Comparison of Lipid Carrier Compositions

Figure 8:
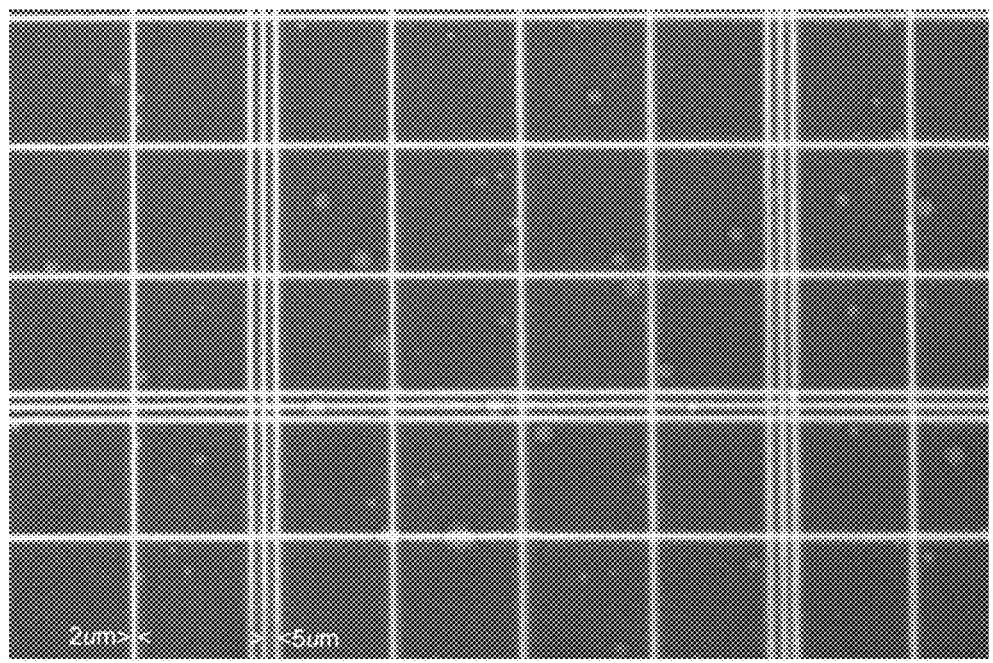

In this example, nebulized fatty acid droplets (nebulized in accordance with aspects and systems of the present disclosure) were impacted on a counting slide and examined, as illustrated in FIG. 8. The pictured flattened, semi-hemispherical droplets in FIG. 8 are more than twice the diameter of the spherical droplets before impact. Oils containing large amounts of linolenic and linoleic fatty acids tend to "flow out" as these fatty acids are natural wetting agents. The droplet population is within the target size distribution of 1-5 μm Mass Median Aerodynamic Diameter (MAMD). The small in-flight droplet size creates imaging difficulties with regard to depth of field at required magnifications for visualization. It is worth noting that the difficulty in measurement of droplets≤5 μm has been acknowledged by many others in the art.

Example 7

Additional Aerosol Formulation Delivery Studies

Animals/Animal Model

Twenty-four adult female sheep were cared for, prepared, and maintained as described in Example 4, above.

Experimental Design

The sheep were randomly assigned to one of the following four groups: 1) Sham and nebulized with flax oil (FO) (not injured, FO-nebulized, n=6); 2) Saline (injured, saline-nebulized, n=6); 3) FO (injured, FO-nebulized, n=6); 4) γ-T+FO (injured, FO+γ-T-nebulized, n=6). Sham animals received no injury but were surgically prepared like treated animals, placed on a ventilator, and given fluid resuscitation and nebulized with 24 ml FO over 47 hr. Saline animals were nebulized with 24 ml of 0.9% NaCl over 47 hr after injury. FO animals were nebulized 24 ml FO over 47 hr after injury. γ-T+FO animals were nebulized 24 ml γ-T+FO mixture solution (γ-T: 1220 mg) over 47 hr after injury.

Aerosol Delivery & Material.

The novel, viscous lipid formulation nebulization nozzle and control system described herein was adapted to a Siemans® 900c servo ventilator (Siemans-Elema AB, Sweden), as shown and discussed generally in relation to FIGS. 1-6B, above. Briefly, for purposes of this particular experiment, the nebulizing nozzle (FIG. 1B) was fabricated from hypodermic needle stock material with a center fluid delivery tube and an outer air delivery tube, in accordance with aspects of the present disclosure. For the purpose of calibration, calibrated blood counting slides were waved through the ventilator inspiratory airflow containing nebulized flax oil formulations allowing droplets to impact onto the slide. The slides were then observed under light microscopy (200×) and sized visually and counted. The vast majority (100:1) of observed impacted deformed and flattened droplets larger than 2 μm and smaller than 10 μm in diameter were conservatively considered to be in the 2-5 μm spherical range.

The output end of the nebulizing nozzle is positioned in the center of flow within the "Y" connector of the ventilator circuit immediately adjacent to and directed toward the tracheostomy tube connector. The nozzle is fed from an air/liquid flow control system adapted to and controlled by the electronic output of the 900c ventilator. The oxygen-air mixer blending the inspired air for the ventilator is tapped to provide the nebulizing air supply providing the nebulization air at the same $FiO_2$ as the ventilator air $FiO_2$. The control cycle timers are programmed to provide 1.0 second of air flow and 0.4 seconds of fluid flow with each inspiration cycle. The fluid flow and subsequent nebulization is configured to occur in the first 0.6 seconds of inspiration thereby providing the nebulized droplets at the beginning of the inspired air flow into the lungs. This nebulizer configuration provides an additional inspired air flow volume of 50 mL/second/breath which was deducted from the total tidal volume.

Cold pressed, filtered flax seed oil (Spectrum Organic Products LLC, Melville, N.Y.) was used alone and as a carrier for 8.3% solution w/w of mixed tocopherols (Decanox™ MTS-90G, a gift from Dr. Brent Flickinger, Archer Daniels Midland Co., Decatur, Ill.) which was measured to contain γ-T (610 mg/g) and, α-T (91 mg/g). The flax oil mixtures were sterile filtered through a 0.22 μm pore filter prior to use. Flax oil alone or flax oil containing 8.3% Decanox™ was administered by continuous pulse nebulization synchronized with the inspiration cycle at a rate of about 0.45-0.5 ml/hour or 11-12 ml/24 hours. Direct lung tissue γ-T concentration measurements (FIG. 9) demonstrated that the aerosolized material was deposited into the lung.

Measured Variables

Arterial and mixed venous blood samples were taken at different time points for measurement of blood gases (IL GEM Premier 3000 Blood Gas Analyzer; GMI, Minnesota). $PaO_2/F_iO_2$ ratio was measured to help assess pulmonary gas exchange. The pulmonary microvascular fluid flux was evaluated by measuring the lung lymph flow. Sheep were sacrificed under deep halothane anesthesia 48 hr after injury. The right lung was then removed, and a 1-cm-thick section was taken from the middle of the lower lobe, injected with 10% formalin, and immersed in formalin. Four tissue samples were taken at predetermined sites for histological examination. Fixed samples were embedded in paraffin, sectioned at 4 μm, and stained with hematoxylin and eosin. A pathologist without knowledge of the group assignments evaluated the lung histology. Levels of airway obstruction were obtained with a standardized protocol. Fifteen bronchi were investigated, and the percentage of area obstructed by the cast was estimated (0%-100%). The remaining lower one-half of the right lower lobe was used for the determination of bloodless wet-to-dry weight ratio. Pulmonary shunt fraction (Qs/Qt) was calculated using standard equations.

γ-tocopherol Measurement

A modification of the method by Podda and colleagues [Podda, M., et al., J. Lipid Res., Vol. 37, pp. 893-901 (1996)] was used for α- and γ-T analyses, as described previously [Morita, N., et al., *SHOCK*, Vol. 25(3), pp. 277-282 (2006)]. Briefly, tissue (~50 mg) or plasma (100 μL) was saponified with alcoholic KOH, extracted with hexane, the extract dried under nitrogen, the residue resuspended in 1:1 ethanol-methanol, then injected into an HPLC system. Tocopherols were detected using an electrochemical detector, and quantitated by comparison to authentic standards. Tissue γ-T levels were adjusted by the wet and dry ratio to correct for the weight change caused by the inflammation and edema.

Malondialdehyde Measurement

Malondialdehyde (MDA) concentrations were utilized to estimate the lipid peroxidation in the lung and were measured as thiobarbituric acid reactive material. Lung tissue MDA levels were quantified with a commercially available assay (Northwest Life Science Specialties, Vancouver, Wash.). The level of lipid peroxides is expressed as MDA per milligram protein, measured using a commercially available assay (Fluka BioChemika, Buchs, Switzerland).

3-Nitotyrosine Measurement

3-Nitrotyrosine concentration, an index of the nitrosylation of proteins, was determined by enzyme-linked immunosorbent assay (ELISA). After the study, samples of lung tissue were collected and homogenates prepared after adding 2 mL of the 10× diluted halogenations buffer (1:10; Cayman Chemical, Ann Arbor, Mich.) containing 250 mM Tris-HCL (pH 7.4), 10 mM EDTA, and 10 mM ethyleneglycol-bis(-aminoethylether)-N,N,N',N'-tetraacetic acid (EGTA). The supernatant was obtained by centrifugation (10,000×g at 4° C.) for 15 min and the supernatant used for assessment. We used the Hycut biotechnology 3-NT solid phase ELISA (Cell Sciences Inc., Canton, Mass.) according to the manufacturer's protocol.

Immunohistochemistry of PARP Activity

For the immunohistochemical detection of poly(ADP-ribose), mouse monoclonal anti-PAR antibody (Calbiochem, San Diego, Calif., USA) (1:1000, overnight, 4° C.) was used after antigen retrieval. Secondary labeling was achieved by using biotinylated horse anti-mouse antibody (Vector Laboratories, Burlingame, Calif., USA) (30 min room temperature). Horseradish peroxidase-conjugated avidin (30 min, room temperature) and brown colored diaminobenzidine (6 min, room temperature) was used to visualize the labeling (Vector Laboratories, Burlingame, Calif., USA). The sections were counterstained with hematoxilin (blue color).

The intensity of PAR staining of individual sections was determined by a blinded experimenter according to a semi-quantitative PAR-positivity score from 1-10. (1: no staining, 2: light cytoplasmic staining, 3: few positive nuclei, 4: light nuclear staining in approximately 10% of cells, 5: light nuclear staining in approximately 25% of cells, 6: light nuclear staining in approximately 50% of cells, 7: strong nuclear staining in approximately 50% of cells, 8: approximately 75% of the nuclei are positive, 9: approximately 90% of the nuclei are positive, 10: few negative cells).

IL-8 and IL-6 mRNA Measurement

Lung tissue was excised at the time of sacrifice and immersed in liquid $N_2$. Total RNA is obtained using a commercially available total RNA purification kit, Purescript™ (Gentra Systems, Inc., Minneapolis, Minn.). Briefly 100 mg of the freshly frozen lung was lysed and homogenized using a mortar and pestle with 3 ml of lysis buffer containing EDTA, citric acid, and SDS according to the manufacturer's protocol, except that the homogenized tissue was incubated overnight at room temperature in the lysis buffer. Precipitation buffer was added and incubated 10 min on ice to precipitate protein and DNA and centrifuged at 3,000 g. The supernatant was placed in 3 ml of isopropanol and centrifuged at 3,000 g for 5 min. The pellet was washed with 3 ml of 70% ethanol, centrifuged again and air-dried for 10 min. The pellet was resuspended in DEPC-treated water. Total RNA was quantitated spectrophotometrically at 260 nm. Quality of the isolated RNA was controlled by measuring the ratio of 28s/18s rRNA. Messenger RNA was isolated from the total RNA by the Straight A's™ mRNA Isolation System (Novagen, Madison, Wis.) purification procedure in which mRNA was first hybridized to oligo dT coupled magnetic beads, washed, and then eluted to obtain polyadenylated mRNA according to the manufacturer's protocol. First strand cDNA was synthesized by reverse transcription of the mRNA samples using MMLV-derived reverse transcriptase (Perkin Elmer, Branchburg, N.J.) and random hexamers for priming according to standard techniques [Sambrook, J., Fritsch, E., and Maniatis, T., "Molecular Cloning: A Laboratory Manual.", Cold Spring Harbor Laboratory Press, New York: (1989)]. The cDNA was then used as a template for real-time PCR. Primers and probes were designed using a commercial online primer design program (Biosearch Technologies, Inc., Novato, Calif.) (Table 5) and purchased from the same company. QPCR was performed with a Rotor-Gene™ 3000 (Corbett Research, San Francisco, Calif.).

TABLE 5

GAPDH, IL-8 and IL-6 Primers and Probes.

| Probe | Conc. | Primer Sequence |
|---|---|---|
| Ov GAPDH Forward | 0.5 μM | 5' CGCTCCCATGTTTGTG 3' |
| Ov GAPDH Reverse | 0.5 μM | 5' GAGGCATTGCTGACA A 3' |
| Ov GAPDH Probe | 62.5 μM | 5' dTGGGCGTGAACCACGAGAAGTATA 3' |

TABLE 5-continued GAPDH, IL-8 and IL-6 Primers and Probes.

| Probe | Conc. | Primer Sequence |
|---|---|---|
| Ov IL-8 Forward | 0.5 µM | 5' GCAACCCTAGACTGCT 3' |
| Ov IL-8 Reverse | 0.5 µM | 5' CCAGTGAAGAATAAAGAAATCG 3' |
| Ov IL-8 Probe | 62.5 µM | 5' TCACGAGTTCCTGTTAACTGTGC 3' |
| Ov IL-6 Forward | 0.5 µM | 5' TTGAGGGAAATCAGGAAA 3' |
| Ov IL-6 Reverse | 0.5 µM | 5' GCTGGAGTGGTTATTAGAC 3' |
| OV IL-6 Probe | 62.5 µM | 5' TCATGGAGTTGCAGAGCAGTATCA 3' |

The reaction mixtures consisted of dilutions of cDNA from 256 ng of RNA, primer and probe concentrations as indicated (Table 5), and subjected to amplification using a final, optimized concentration of $MgCl_2$, 0.375 U of Taq polymerase (AmpliTaq®, Perkin-Elmer) and 0.2 mM dTP's in a reaction volume of 15 µl. The mixtures were amplified for 40 cycles at a melting temperature of 95° C. for 10 min, an annealing temperature of 55° C. for 10 s, and extension at 60° C. for 45 s. The threshold amplifications (Ct) for each dilution, and reaction efficiencies were determined for each analyte using Rotor-Gene™ software (Corbett Research). The copy numbers were normalized between samples using GAPDH copy numbers obtained by determination of GAPDH copy number using an external standard constructed from the v-erb gene. All results were expressed as copy numbers per µg of total RNA.

Statistical Analysis

Summary statistics of data are expressed as means±standard error of the mean. Statistical significance was determined using a two-factor analysis of variance with repeated measures. The two factors were treatment and time. Fisher's least significant difference procedure with Bonferoni's adjustment for number of comparisons is used for the multiple comparisons (or post-hoc analysis). Effects and interactions were assessed at the $p<0.05$ level of significance.

Results

All animals survived the 48 h experimental period after the combined injury with 40% TBSA burn and smoke inhalation. There were no statistically significant differences in the mean arterial carboxyhemoglobin levels measured immediately after smoke exposure between the saline, FO and γ-T+FO groups (67.4%±6%, 77.0%±5% and 68%±7%, respectively). Since vitamin E may decrease platelet adhesion, the clotting time was evaluated. The γ-T treatment did not result in a bleeding tendency in any of the groups. The activated clotting time was 144±14 s at baseline, 163±3 s at 24 hr, and 160±10 s at 48 hr in the γ-T+FO group and 158±3 s at baseline, 177±10 s at 24 hr, and 183±12 s at 48 hr in the nebulized saline group.

The lung contains primarily α-T and relatively low γ-T concentrations in sheep. Lung γ-T concentrations were low, and as shown previously, burn and smoke inhalation injury further reduced both α- and γ-T concentrations in lung tissue. However, the nebulization significantly increased γ-T concentrations in lungs of sheep in the γ-T+FO group. No increases were found in plasma γ-T (data not shown) documenting that the γ-T administration is confined to the lung.

Table 6 shows a comparison of effects of FO or γ-T+FO nebulization on pulmonary gas exchange ($PaO_2/FiO_2$ ratio and Qs/Qt) and pulmonary transvascular fluid flux (lung lymph flow). There was a significant decrease in $PaO_2/FiO_2$ and an increase in pulmonary shunt fraction and lung lymph flow in the saline group resulting from the combined burn and smoke inhalation injury as compared with the sham group at 24, 36, and 48 hr. FO nebulization had a tendency to attenuate the changes seen in animals with the saline group. As compared with the FO group, the use of nebulized γ-T+FO significantly improved the $PaO_2/FiO_2$ at 36 hr and in lung lymph flow at 24 hr and 48 hr. $PaO_2/FiO_2$ ratio (FIG. 10A) was markedly decreased in animals that were nebulized with saline (injured) as compared with sham animals (uninjured). Nebulization of γ-T+FO attenuated the decrease in this variable. Statistically significant differences were observed at 24, 30, 36, 42 and 48 hr compared with the saline group and at 30, 36, and 42 hr compared with FO group. An increase in pulmonary shunt fraction (FIG. 10B) seen in the saline group was significantly attenuated by FO nebulization at 48 hr and γ-T+FO nebulization at 36, 42 and 48 hr after the combined injury.

TABLE 6

Pulmonary Gas Exchange and Transvascular Fluid Flux Results.

| | Time (hours, h) | | | | | |
|---|---|---|---|---|---|---|
| | 0 | 6 | 12 | 24 | 36 | 48 |
| $PaO_2/FiO_2$ | | | | | | |
| Sham | 487 ± 14 | 575 ± 24 | 560 ± 19 | 575 ± 14 | 558 ± 15 | 560 ± 11 |
| Saline | 492 ± 16 | 467 ± 63 | 443 ± 35 | 174 ± 31* | 117 ± 30* | 81 ± 17* |
| FO | 486 ± 16 | 525 ± 28 | 416 ± 59 | 290 ± 65* | 194 ± 40* | 137 ± 24* |
| γ-T + FO | 490 ± 13 | 523 ± 41 | 440 ± 64 | 415 ± 55*† | 349 ± 48*†‡ | 270 ± 48*† |
| Qs/Qt | | | | | | |
| Sham | 0.19 ± 0.02 | 0.12 ± 0.01 | 0.15 ± 0.01 | 0.14 ± 0.01 | 0.13 ± 0.01 | 0.14 ± 0.01 |
| Saline | 0.19 ± 0.04 | 0.14 ± 0.03 | 0.15 ± 0.02 | 0.33 ± 0.05* | 0.41 ± 0.07* | 0.49 ± 0.07 |
| FO | 0.17 ± 0.09 | 0.14 ± 0.02 | 0.18 ± 0.03 | 0.24 ± 0.04 | 0.30 ± 0.06* | 0.33 ± 0.06*† |
| γ-T + FO | 0.18 ± 0.01 | 0.14 ± 0.01 | 0.20 ± 0.03 | 0.23 ± 0.05 | 0.23 ± 0.03† | 0.26 ± 0.03† |

TABLE 6-continued

Pulmonary Gas Exchange and Transvascular Fluid Flux Results.

| | Time (hours, h) | | | | | |
|---|---|---|---|---|---|---|
| | 0 | 6 | 12 | 24 | 36 | 48 |
| Lymph | | | | | | |
| Sham | 2.8 ± 0.7 | 3.5 ± 0.6 | 3.1 ± 0.6 | 3.7 ± 1.4 | 2.8 ± 0.8 | 3.2 ± 0.7 |
| Saline | 4.8 ± 0.9 | 11.8 ± 1.8 | 19.6 ± 5.1 | 42.7 ± 6.0* | 46.5 ± 4.1* | 48.2 ± 1.9* |
| FO | 6.8 ± 2.0 | 9.4 ± 2.2 | 14.4 ± 3.4 | 23.5 ± 7.5*† | 23.5 ± 7.1*† | 26.9 ± 5.9*† |
| γ-T + FO | 4.1 ± 1.17 | 9.9 ± 4.3 | 9.24 ± 3.3 | 8.6 ± 2.8†‡ | 9.1 ± 2.5† | 10.5 ± 2.2†‡ |

Data are expressed as means ± SEM.
*P < 0.05 vs. Sham.
†P < 0.05 vs. Saline;
‡P < 0.05 vs. FO.

Lung lymph flow, a characteristic of pulmonary transvascular fluid flux, was markedly increased in injured, saline nebulized animals compared with the sham group (FIG. 11). The lymph flow began to increase 12 hr after the insult and a peak was observed at 42 hr. However, nebulization of γ-T+FO reversed this increase in pulmonary transvascular fluid flux and significant differences were observed between γ-T+FO and Saline groups at 18, 24, 30, 36, 42 and 48 hr, and γ-T+FO and FO groups at 24 and 48 hr after the combined injury. Lung bloodless wet-to-dry weight ratio, a measure of lung water content, was significantly increased at 48 hr after insult in the saline group as compared with the sham group (FIG. 12A). However, the nebulization of γ-T+FO significantly reduced this increase.

The airway obstruction score revealed a significant increase in mean obstruction of bronchi (FIG. 12B) in the saline group as compared with the sham group. Treatment with γ-T+FO nebulization significantly reduced the obstruction score.

FIG. 13A illustrates the effect of γ-T+FO nebulization on malondialdehyde concentration which is an index of lipid peroxidation (ROS) in lung tissue. Malondialdehyde concentration was significantly increased in the saline group as compared with the sham group. Malondialdehyde levels did not markedly increase in animals treated with γ-T+FO nebulization.

3-Nitrotyrosine is a marker of nitrosative stress, resulting from reactive nitrogen species (RNS) such as peroxynitrite. Burn and smoke injury caused a marked increase in lung 3-nitrotyrosine 48 h after the insults. γ-T+FO nebulization significantly prevented the increase in 3-nitrotyrosine (FIG. 13B).

After burn and smoke injury, there was a marked increase in poly (ADP-ribose) reactivity in the Saline and FO groups (FIGS. 14A-14B). Treatment with γ-T+FO nebulization prevented this increase in activity (FIG. 14A). FIG. 14B shows the PAR-positivity score graph which quantified the degree of poly (ADP-ribose) histochemical stain. Burn and smoke injury caused a significant increase in lung poly (ADP-ribose) polymerase activity. However, γ-T+FO nebulization significantly prevented the increase in lung poly (ADP-ribose) polymerase activity.

To determine the pro-inflammatory chemokines, IL-8 and IL-6 mRNA were measured in lung tissue (FIG. 15). Burn and smoke injury caused a marked increase in lung IL-8 and IL-6 mRNA 48 hr after the insults. γ-T+FO nebulization prevented the increase in IL-8 and IL-6 mRNA (FIG. 15).

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intends to protect all such modifications and improvements to the full extent that such falls within the scope or range of equivalent of the following claims.

All of the methods, processes and/or apparatus disclosed and claimed herein can be made and executed without undue experimentation in light of the present disclosure. While the methods, apparatus and processes of this invention have been described in terms of preferred embodiments, it will be apparent to those of skill in the art that variations may be applied to the methods, apparatus and/or processes and in the steps or in the sequence of steps of the methods described herein without departing from the concept and scope of the invention. For example, while objects of the present invention have been described as being in specific spatial relationships such as "parallel to" and "horizontal to", it is envisioned that such objects can also be at a variety of angles (e.g., acute, obtuse, or oblique angles) with respect to one another without departing from the scope of the present invention. More specifically, it will be apparent that certain features which are both mechanically and functionally related can be substituted for the features described herein while the same or similar results would be achieved. All such similar substitutes and modifications apparent to those skilled in the art are deemed to be within the scope and concept of the invention.

Further, any documents to which reference is made in the application for this patent as well as all references listed in any list of references filed with the application are hereby incorporated by reference. However, to the extent statements might be considered inconsistent with the patenting of this invention such statements are expressly not to be considered as made by the applicant(s).

What is claimed is:

1. A pulmonary drug delivery system capable of nebulizing a drug composition comprising a water-insoluble or substantially water-insoluble drug and a fatty acid or lipid, the system comprising:
   a carrier gas reservoir;
   a drug reservoir comprising a flexible bladder that is disposed within the carrier gas reservoir and that is able to be pressurized by gas within the carrier gas reservoir;
   a face mask; and
   a nebulizing nozzle in fluid communication with face mask, the drug reservoir and the carrier gas reservoir, wherein the nebulizing nozzle comprises an outer carrier gas delivery tube spaced apart from and disposed around at least one inner drug delivery tube and wherein the outer carrier gas delivery tube and the at least one inner drug delivery tube(s) share a longitudinal axis and are together dimensioned and disposed such that expulsion of a carrier gas through the outer carrier gas delivery tube forms an outer surrounding stream of carrier gas that carries an inner flow of fluid from the drug reservoir in a center of carrier gas flow exiting the nebulizing nozzle and thereby produces aerosol drug containing droplets having a particle size ranging from about 2 μm to about 12 μm in median mass aerodynamic size that are delivered to a patient via a mouth and/or nose of the patient.

2. The pulmonary drug delivery system of claim 1, further comprising a mechanical ventilator.

3. The pulmonary drug delivery system of claim 2, wherein the mechanical ventilator is configured to synchronize a cyclic nebulization of the aerosol drug containing droplets.

4. The pulmonary drug delivery system of claim 1, wherein the nebulizing nozzle can produce aerosol drug containing droplets having a particle size ranging from about 2 μm to about 5 μm.

5. The pulmonary drug delivery system of claim 1, wherein the nozzle has an air volume to nebulized droplet volume ratio less than about 60,000:1.

6. The pulmonary drug delivery system of claim 5, wherein the nozzle has an air volume to nebulized droplet volume ratio less than about 15,000:1.

7. The pulmonary drug delivery system of claim 1, wherein an intermediate air space between the outer carrier gas delivery tube and the inner drug delivery tube ranges from about 0.000009 in$^2$ to about 0.001 in$^2$.

8. The pulmonary drug delivery system of claim 7, wherein an intermediate air space between the outer carrier gas delivery tube and the inner drug delivery tube ranges from about 0.00000259 in$^2$ to about 0.001 in$^2$.

9. The pulmonary drug delivery system of claim 1, wherein the outer carrier gas delivery tube has an inner diameter ranging from about 0.01 inches to about 0.05 inches.

10. The pulmonary drug delivery system of claim 1, wherein the outer gas delivery tube is disposed around a plurality of individual inner drug delivery tubes disposed within, and sharing a longitudinal axis with, the outer gas delivery tube.

11. The pulmonary drug delivery system of claim 10, wherein the plurality of individual drug delivery tubes ranges from 2 to 12 individual drug delivery tubes disposed within the outer gas delivery tube.

12. The pulmonary drug delivery system of claim 10, where the relative dimensions of the outer gas delivery tube and the plurality of individual inner drug delivery tubes produce the aerosol drug containing droplets having a particle size ranging from about 2 μm to about 12 μm in median mass aerodynamic size.

13. A pulmonary drug delivery system capable of nebulizing a drug composition comprising a water-insoluble or substantially water-insoluble drug and a fatty acid or lipid, the system comprising:
    a drug reservoir;
    a carrier gas reservoir;
    a face mask; and
    a nebulizing nozzle in fluid communication with face mask, the drug reservoir and the carrier gas reservoir, wherein the nebulizing nozzle comprises an outer carrier gas delivery tube spaced apart from and disposed around at least one inner drug delivery tube and wherein the outer carrier gas delivery tube and the at least one inner drug delivery tube(s) share a longitudinal axis and are together dimensioned and disposed such that expulsion of a carrier gas through the outer carrier gas delivery tube forms an outer surrounding stream of carrier gas that carries an inner flow of fluid from the drug reservoir in a center of carrier gas flow exiting the nebulizing nozzle and thereby produces aerosol drug containing droplets having a particle size ranging from about 2 μm to about 12 μm in median mass aerodynamic size that are delivered to a patient via a mouth and/or nose of the patient, wherein the drug reservoir is disposed within a pressurization chamber that is adapted to force delivery of a drug from the drug reservoir into the drug delivery tube and wherein the pressurization chamber can be pressurized by the carrier gas reservoir.

14. The pulmonary drug delivery system of claim 13, further comprising a spring loaded flow valve positioned and adapted to control pressurization by the carrier gas reservoir.

15. The pulmonary drug delivery system of claim 13, further comprising a spring loaded blow-off valve positioned and adapted to prevent excess pressure in the pressurization chamber.

16. A pulmonary drug delivery system capable of nebulizing a drug composition comprising a water-insoluble or substantially water-insoluble drug and a fatty acid or lipid, the system comprising:
    a nebulizing nozzle in fluid communication with a drug reservoir that is disposed within a carrier gas reservoir, wherein the drug reservoir is adapted to be pressurized by gas within the carrier gas reservoir and thereby force delivery of a drug from the drug reservoir into the nebulizing nozzle, and
    wherein the nebulizing nozzle comprises an outer carrier gas delivery tube spaced apart from and disposed around at least one inner drug delivery tube and wherein the outer carrier gas delivery tube and the at least one inner drug delivery tube(s) share a longitudinal axis and are together dimensioned and disposed such that expulsion of a carrier gas through the outer carrier gas delivery tube forms an outer surrounding stream of carrier gas that carries an inner flow of fluid from the drug reservoir in a center of carrier gas flow exiting the nebulizing nozzle and thereby produces aerosol drug containing droplets having a particle size ranging from about 2 μm to about 12 μm in median mass aerodynamic size.

17. The pulmonary drug delivery system of claim 16, wherein the drug reservoir is a flexible bladder that is disposed within the carrier gas reservoir.

18. The pulmonary drug delivery system of claim 16, further comprising a spring loaded flow valve positioned and adapted to control pressurization by the carrier gas reservoir.

19. The pulmonary drug delivery system of claim 16, further comprising a spring loaded blow-off valve positioned and adapted to prevent excess pressure in the pressurization chamber.

* * * * *